(12) United States Patent
Mittelman et al.

(10) Patent No.: US 9,916,416 B2
(45) Date of Patent: Mar. 13, 2018

(54) SYSTEM AND METHOD FOR GENOTYPING USING INFORMED ERROR PROFILES

(71) Applicant: Virginia Tech Intellectual Properties, Inc., Blacksburg, VA (US)

(72) Inventors: David A. Mittelman, Blacksburg, VA (US); Christopher T. Franck, Blacksburg, VA (US)

(73) Assignee: VIRGINIA TECH INTELLECTUAL PROPERTIES, INC., Blacksburg, VA (US)

(*) Notice: Subject to any disclaimer, the term of this patent is extended or adjusted under 35 U.S.C. 154(b) by 949 days.

(21) Appl. No.: 14/057,216

(22) Filed: Oct. 18, 2013

(65) Prior Publication Data

US 2014/0114582 A1    Apr. 24, 2014

Related U.S. Application Data

(60) Provisional application No. 61/715,581, filed on Oct. 18, 2012.

(51) Int. Cl.
*G06F 19/10* (2011.01)
*G06F 19/00* (2011.01)
*G06F 19/18* (2011.01)

(52) U.S. Cl.
CPC .................................. *G06F 19/18* (2013.01)

(58) Field of Classification Search
None
See application file for complete search history.

(56) References Cited

U.S. PATENT DOCUMENTS

| | | |
|---|---|---|
| 6,850,846 B2 | 2/2005 | Wang et al. |
| 8,428,886 B2 | 4/2013 | Wong et al. |

OTHER PUBLICATIONS

Nielsen et al. (Nature Reviews/Genetics (2011) vol. 12:443-451).*
1000 Genomes Project Consortium. A map of human genome variation from population-scale sequencing. Nature. 2010;467:1061-1073.
Albers CA, Lunter G, Macarthur DG, McVean G, Ouwehand WH, et al. Dindel: Accurate indel calls from short-read data. Genome research. 2011;21:961-973.
Albrecht A, Mundlos S. The other trinucleotide repeat: polyalanine expansion disorders. Curr. Opin. Genet. Dev. 2005;15:285-293.
Albrecht AN, Kornak U, Boddrich A, Suring K, Robinson PN, et al. A molecular pathogenesis for transcription factor associated poly-alanine tract expansions. Human molecular genetics. 2004;13:2351-2359.
Altshuler DM, Gibbs RA, Peltonen L, Dermitzakis E, Schaffner SF, et al. Integrating common and rare genetic variation in diverse human populations. Nature. 2010;467:52-58.
Axford MM, Lopez-Castel A, Nakamori M, Thornton CA, Pearson CE. Replacement of the myotonic dystrophy type 1 CTG repeat with 'non-CTG repeat' insertions in specific tissues. Journal of medical genetics. 2011;48:438-443.
Bashir A, Volik S, Collins C, Bafna V, Raphael BJ. Evaluation of paired-end sequencing strategies for detection of genome rearrangements in cancer. PLoS computational biology. 2008;4:e1000051, pp. 1-14.
Benson G. Tandem repeats finder: a program to analyze DNA sequences. Nucleic acids research. 1999;27:573-580.
Challis D, Yu J, Evani US, Jackson AR, Paithankar S, Coarfa C, Milosavljevic A, Gibbs RA, Yu F. An integrative variant analysis suite for whole exome next-generation sequencing data. BMC Bioinformatics. 2012;13:8.
Danecek P, Auton A, Abecasis G, Albers CA, Banks E, DePristo MA, Handsaker RE, Lunter G, Marth GT, Sherry ST, et al. The variant call format and VCFtools. Bioinformatics. 2011;27:2156-2158.
DePristo MA, Banks E, Poplin R, Garimella KV, Maguire JR, Hartl C, Philippakis AA, del Angel G, Rivas MA, Hanna M, et al. A framework for variation discovery and genotyping using next-generation DNA sequencing data. Nat. Genet. 2011;43:491-498.
Douglas JA, Skol AD, Boehnke M. Probability of detection of genotyping errors and mutations as inheritance inconsistencies in nuclear-family data. Am. J. Hum. Genet. 2002;70:487-495.
Ewing B, Hillier L, Wendl MC, Green P. (1998): Base-calling of automated sequencer traces using phred. I. Accuracy assessment. Genome Res. 8(3):175-185.
Ewing B, Green P. (1998): Base-calling of automated sequencer traces using phred. II. Error probabilities. Genome Res. 8(3):186-194.
Fondon JW, III, Martin A, Richards S, Gibbs RA, Mittelman D. Analysis of microsatellite variation in *Drosophila melanogaster* with population-scale genome sequencing. PLoS One. 2012;7:e33036, pp. 1-9.
Fondon JW, 3rd, Mele GM, Brezinschek RI, Cummings D, Pande A, et al. Computerized polymorphic marker identification: experimental validation and a predicted human polymorphism catalog. Proceedings of the National Academy of Sciences of the United States of America. 1998;95:7514-7519.
Fonville NC, Ward RM, Mittelman D. Stress-induced modulators of repeat instability and genome evolution. J. Mol. Microbiol. Biotechnol. 2011;21:36-44.
Ge J, Eisenberg A, Budowle B. Developing criteria and data to determine best options for expanding the core CODIS loci. Investig. Genet. 2012;3:1, pp. 1-14.
Gemayel R, Vinces MD, Legendre M, Verstrepen KJ. Variable tandem repeats accelerate evolution of coding and regulatory sequences. Annual review of genetics. 2010;44:445-477.
Gerber HP, Seipel K, Georgiev O, Hofferer M, Hug M, et al. Transcriptional activation modulated by homopolymeric glutamine and proline stretches. Science. 1994;263:808-811.
Glen CD, Dubrova YE. Exposure to anticancer drugs can result in transgenerational genomic instability in mice. Proc. Natl. Acad. Sci. USA. 2012;109:2984-2988.

(Continued)

*Primary Examiner* — Lori A Clow
(74) *Attorney, Agent, or Firm* — Daniel A. Blasiole; Charles S. Sara; DeWitt Ross & Stevens S.C.

(57) ABSTRACT

A system and method for genotyping tandem repeats in sequencing data. The invention uses Bayesian model selection guided by an empirically-derived error model that incorporates properties of sequence reads and reference sequences to which they map.

8 Claims, 13 Drawing Sheets

(56) References Cited

OTHER PUBLICATIONS

Gymrek M, Golan D, Rosset S, Erlich Y. lobSTR: a short tandem repeat profiler for personal genomes. Genome Res. 2012;22:1154-1162.

Hannan AJ. Tandem repeat polymorphisms: modulators of disease susceptibility and candidates for 'missing heritability'. Trends in genetics: TIG. 2010;26:59-65.

Highnam G, Franck C, Martin A, Stephens C, Puthige A, Mittelman D. Accurate human microsatellite genotypes from high-throughput resequencing data using informed error profiles. Nucleic Acids Res. Jan. 7, 2013;41(1):e32.

Hile SE, Eckert KA. DNA polymerase kappa produces interrupted mutations and displays polar pausing within mononucleotide microsatellite sequences. Nucleic acids research. 2008;36:688-696.

Kelkar YD, Strubczewski N, Hile SE, Chiaromonte F, Eckert KA, et al. What is a microsatellite: a computational and experimental definition based upon repeat mutational behavior at A/T and GT/AC repeats. Genome biology and evolution. 2010;2:620-635.

Korol A, Rashkovetsky E, Iliadi K, Nevo E. *Drosophila* flies in "Evolution Canyon" as a model for incipient sympatric speciation. Proc Natl Acad Sci U S A. 2006;103:18184-18189.

Langmead B, Salzberg SL. Fast gapped-read alignment with Bowtie 2. Nat. Methods. 2012;9:357-359.

Lango Allen H, Estrada K, Lettre G, Berndt SI, Weedon MN, et al. Hundreds of variants clustered in genomic loci and biological pathways affect human height. Nature. 2010;467:832-838.

Legendre M, Pochet N, Pak T, Verstrepen KJ. Sequence-based estimation of minisatellite and microsatellite repeat variability. Genome Res. 2007;17:1787-1796.

Li H, Durbin R. Fast and accurate long-read alignment with Burrows-Wheeler transform. Bioinformatics. 2010;26:589-595.

Li H, Handsaker B, Wysoker A, Fennell T, Ruan J, Homer N, Marth G, Abecasis G, Durbin R. The Sequence Alignment/Map format and SAMtools. Bioinformatics. 2009;25:2078-2079.

Li H, Homer N. A survey of sequence alignment algorithms for next-generation sequencing. Brief. Bioinform. 2010;11:473-483.

Li H, Durbin R. Fast and accurate short read alignment with Burrows-Wheeler transform. Bioinformatics. 2009;25:1754-1760.

Li H, Ruan J, Durbin R. Mapping short DNA sequencing reads and calling variants using mapping quality scores. Genome research. 2008;18:1851-1858.

Loeb LA, Loeb KR, Anderson JP. Multiple mutations and cancer. Proc. Natl. Acad. Sci. USA. 2003;100:776-781.

Lopez Castel A, Cleary JD, Pearson CE. Repeat instability as the basis for human diseases and as a potential target for therapy. Nat. Rev. Mol. Cell Biol. 2010;11:165-170.

Lunter G, Goodson M. Stampy: a statistical algorithm for sensitive and fast mapping of Illumina sequence reads. Genome Res. 2011;21:936-939.

Lynch HT, Lynch PM, Lanspa SJ, Snyder CL, Lynch JF, et al. Review of the Lynch syndrome: history, molecular genetics, screening, differential diagnosis, and medicolegal ramifications. Clinical genetics. 2009;76:1-18.

Mackay TFC, Richards S, Stone EA, Barbadilla A, Ayroles JF, Zhu D, Casillas S, Han Y, Magwire MM, Cridland JM, et al. The *Drosophila melanogaster* Genetic Reference Panel. Nature. 2012;482:173-178.

Manolio TA, Collins FS, Cox NJ, Goldstein DB, Hindorff LA, et al. Finding the missing heritability of complex diseases. Nature. 2009;461:747-753.

Margulies M, Egholm M, Altman WE, Attiya S, Bader JS, et al. Genome sequencing in microfabricated high-density picolitre reactors. Nature. 2005;437:376-380.

McIver LJ, Fondon JW, 3rd, Skinner MA, Garner HR. Evaluation of microsatellite variation in the 1000 Genomes Project pilot studies is indicative of the quality and utility of the raw data and alignments. Genomics. 2011;97:193-199.

Mills RE, Luttig CT, Larkins CE, Beauchamp A, Tsui C, et al. An initial map of insertion and deletion (INDEL) variation in the human genome. Genome research. 2006;16:1182-1190.

Mills RE, Walter K, Stewart C, Handsaker RE, Chen K, et al. Mapping copy number variation by population-scale genome sequencing. Nature. 2011;470:59-65.

Mills RE, Pittard WS, Mullaney JM, Farooq U, Creasy TH, et al. Natural genetic variation caused by small insertions and deletions in the human genome. Genome research. 2011;21:830-839.

Mirkin SM. Expandable DNA repeats and human disease. Nature. 2007;447:932-940.

Mittelman D, Moye C, Morton J, Sykoudis K, Lin Y, et al. Zinc-finger directed double-strand breaks within CAG repeat tracts promote repeat instability in human cells. Proceedings of the National Academy of Sciences of the United States of America. 2009;106:9607-9612.

Orr HT. Unstable nucleotide repeat minireview series: a molecular biography of unstable repeat disorders. The Journal of biological chemistry. 2009;284:7405.

Reuschenbach M, Kloor M, Morak M, Wentzensen N, Germann A, et al. Serum antibodies against frameshift peptides in microsatellite unstable colorectal cancer patients with Lynch syndrome. Familial cancer. 2010;9:173-179.

Sainudiin R, Durrett RT, Aquadro CF, Nielsen R. Microsatellite mutation models: insights from a comparison of humans and chimpanzees. Genetics. 2004;168:383-395.

Sawyer LA, Hennessy JM, Peixoto AA, Rosato E, Parkinson H, et al. Natural variation in a *Drosophila* clock gene and temperature compensation. Science. 1997;278:2117-2120.

Schug MD, Mackay TF, Aquadro CF. Low mutation rates of microsatellite loci in *Drosophila melanogaster*. Nature genetics. 1997;15:99-102.

TCGA. Comprehensive genomic characterization defines human glioblastoma genes and core pathways. Nature. 2008;455:1061-1068.

Verstrepen KJ, Jansen A, Lewitter F, Fink GR. Intragenic tandem repeats generate functional variability. Nature genetics. 2005;37:986-990.

Wells RD, Dere R, Hebert ML, Napierala M, Son LS. Advances in mechanisms of genetic instability related to hereditary neurological diseases. Nucleic acids research. 2005;33:3785-3798.

Vinces MD, Legendre M, Caldara M, Hagihara M, Verstrepen KJ. Unstable tandem repeats in promoters confer transcriptional evolvability. Science. 2009;324:1213-1216.

\* cited by examiner

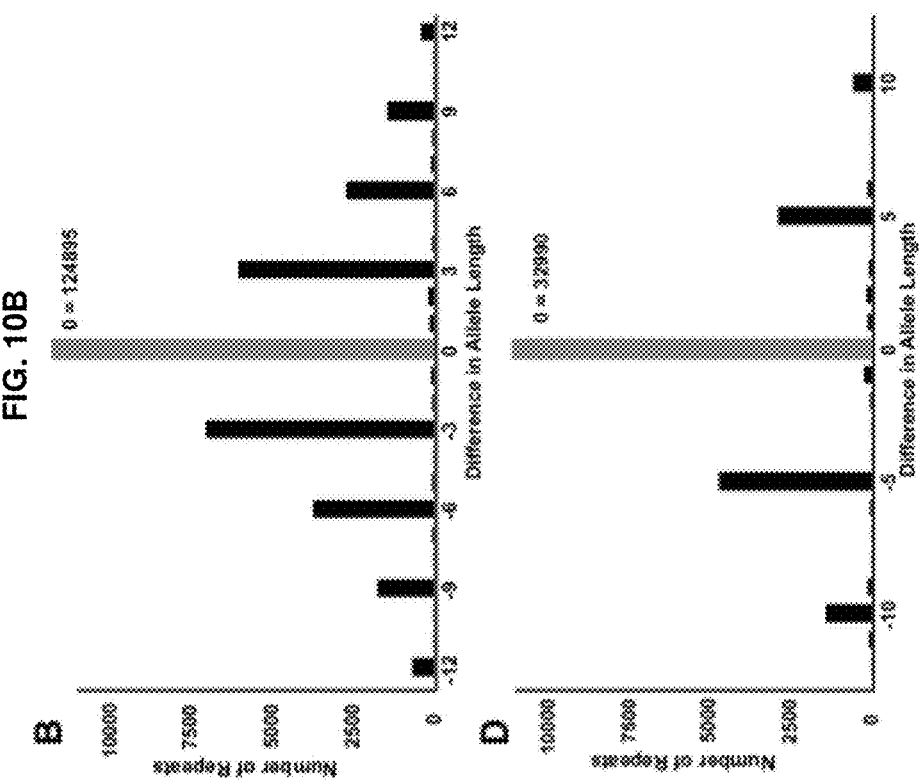
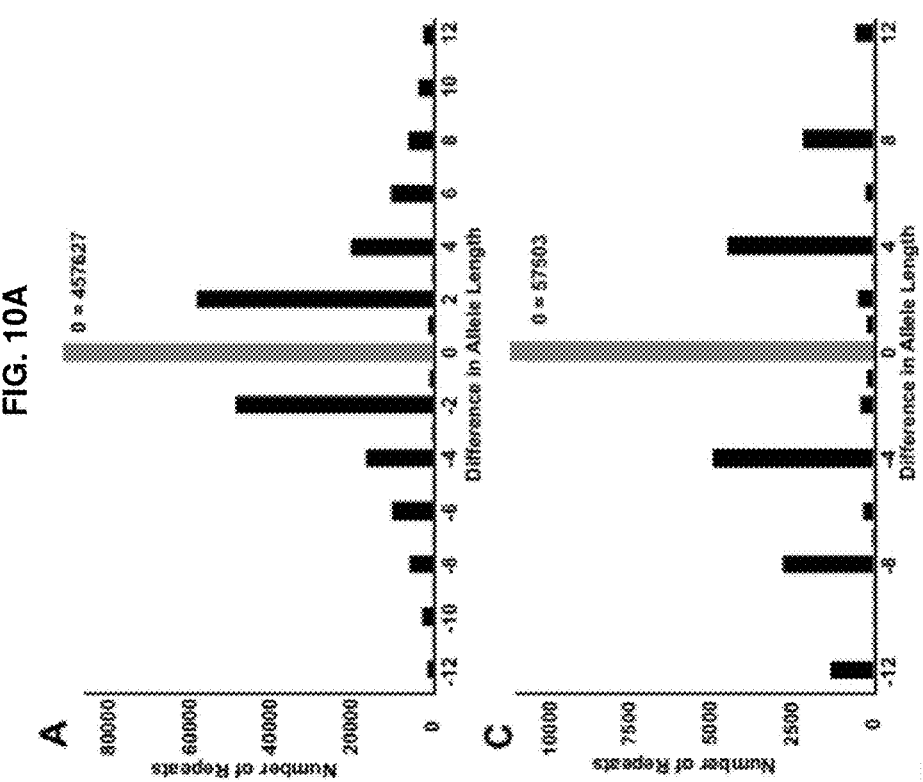
FIG. 10A
FIG. 10B
FIG. 10C
FIG. 10D

SYSTEM AND METHOD FOR GENOTYPING USING INFORMED ERROR PROFILES

CROSS-REFERENCE TO RELATED APPLICATIONS

This application claims priority under 35 USC § 119(e) to U.S. Provisional Patent Application 61/715,581 filed Oct. 18, 2012, the entirety of which is incorporated herein by reference.

FIELD OF THE INVENTION

The present invention is directed to a system and method of genotyping with sequencing data. The present invention is more specifically directed to a system and method of genotyping tandem repeats, such as microsatellites.

BACKGROUND

Tandem repeats are dispersed throughout the genome, in and around gene regions. They were first identified as agents of disease ~20 years ago (Mirkin et al.), and since then, several microsatellite repeats (not all of which are triplets) have been identified as the underlying basis for a wide range of neurological and morphological disorders in humans and other mammals (Lopez et al., Orr et al., Albrecht et al. 2005). In addition to causing disease, microsatellites can exert subtle effects on gene function and quantitative traits (reviewed in Gemayel et al.). Repeats are also mutational hotspots in that their instability can be triggered by nearly any aspect of DNA metabolism, and even transcription or stress (reviewed in Fonville et al.). This sensitivity to defects in repair and cellular insults makes repeats useful markers for genome instability and cancer (Glen et al., Loeb et al.). Further, analyzing repeats in personal genomes promises benefit not just to medical genetics and the diagnosis of repeat-related disorders but also to forensics and genealogy, where shorter and more stable tandem repeats can serve as DNA fingerprints to uniquely identify individuals (Ge et al., Gymrek et al.). The use of accurately and globally measuring tandem repeats spans medicine, genetics and biotechnology; repeats influence clinical and subclinical phenotypes, are signatures for genomic instability and cancer, and are important markers for forensics and genealogy.

Despite their use and biological importance, some repetitive sequences (particularly microsatellites) are challenging to study with short-read sequencing technology, such as next-generation sequencing technology. Genotyping microsatellite repeats from reference-mapped reads is fundamentally distinct from calling SNPs or indels in non-repetitive sequence because there is no sound basis for inferring homology between pairs of aligned repeat units.

Current approaches for identifying repeat mutations include indel genotyping methods implemented in popular software suites, such as GATK (DePristo et al.) and ATLAS2 (Challis et al.), that can reveal indels within repeat regions or the recently reported lobSTR method (Gymrek et al.). Indel callers are ill-suited for identifying repeat mutation. As they do not report repeat genotypes, they can base indel identification on reads that do not fully span the repeat. They also fail to account for the error rates of different repeat types. The mutation rate of microsatellite repeats is influenced largely not only by the length of repeat tract but also by other intrinsic properties, such as the size of the repeated unit and the purity (lack of interruptions) of the repeated sequence (Legendre et al.). A genotyping method that incorporates the mutational properties of repeat sequences will be better able to distinguish false alleles from true heterozygosity. However, the success of a genotyping approach relies on more than just the accurate identification of true alleles—the method must be applicable to the greatest number of loci genome-wide. The lobSTR method, for example, makes microsatellite calls genome-wide (Gymrek et al.); however, it is blind to homopolymers runs (i.e. mononucleotide repeats, which are a common and important source of genetic variation).

Systems and methods that accurately genotype microsatellite repeats are needed.

SUMMARY OF THE INVENTION

The present invention is a system and method for genotyping microsatellite repetitive sequences in whole genome sequencing data. The present invention combines a repeat-aware method for repeat allele determination with a Bayesian genotyping approach that uses an empirically-derived error model informed by properties of a repeat sequence and the sequence reads that map to it. The invention is particularly suited for use with next-generation sequencing data.

One version of the invention comprises a method of genotyping. A first step includes obtaining a sequence-read mapping. The sequence-read mapping comprises sequence reads from a subject polynucleotide sequence mapped to a reference sequence. An additional step includes selecting flanking reads from the sequence reads. Each flanking read spans a repeat in the reference sequence in addition to one or more flanking bases on each of two ends of the repeat. Selecting the flanking reads from the sequence reads results in a flanking-read mapping comprising the repeat and the flanking reads that map thereto. A further step includes extracting a sequence attribute from the flanking-read mapping. A further step includes associating the extracted sequence attribute with a genotyping error rate. A further step includes calculating a genotype probability for each flanking read from the genotyping error rate. A further step includes assigning a genotype to the subject polynucleotide sequence based on the genotype probabilities calculated for the flanking reads, wherein the genotype comprises a characteristic of a most probable of the flanking reads. In some versions, the genotype comprises a repeat length.

The extracted sequence attribute may be selected from the group consisting of repeat length, repeat unit size, repeat unit sequence, repeat purity, number of flanking-read flanking bases on each end of the flanking read, number of exact matches between the flanking-read flanking bases and the flanking bases on the reference sequence, flanking-read length, flanking-base sequence, number of flanking sequences mapped per repeat, number of substitutions in the flanking read with respect to the reference sequence, number of insertions in the flanking read with respect to the reference sequence, number of total indels in the flanking read with respect to the reference sequence, number of substitutions in the flanking-read repeat with respect to the repeat in the reference sequence, number of insertions in the flanking-read repeat with respect to the repeat in the reference sequence, number of total indels in the flanking-read repeat with respect to the repeat in the reference sequence, number of substitutions in the flanking-read flanking bases with respect to the flanking bases in the reference sequence, number of insertions in the flanking-read flanking bases with respect to the flanking bases in the reference sequence, number of total indels in the flanking-read flanking bases with respect to the flanking bases in the reference sequence, average base quality score of the flanking read, and mapping quality score. In some versions, the extracted sequence attribute is selected from the group consisting of repeat length, repeat unit size, and average base quality score of the flanking read.

In some versions, associating the extracted sequence attribute with the genotyping error rate comprises matching the sequence attribute with one of a plurality of bins of partitioned sequence attribute values with known, corresponding genotyping error rates. Each of the plurality of bins may encompass a different value or plurality of values for a sequence attribute selected from the group consisting of repeat length, repeat unit size, repeat unit sequence, repeat purity, number of flanking-read flanking bases on each end of the flanking read, number of exact matches between the flanking-read flanking bases and the flanking bases on the reference sequence, flanking-read length, flanking-base sequence, number of flanking sequences mapped per repeat, number of substitutions in the flanking read with respect to the reference sequence, number of insertions in the flanking read with respect to the reference sequence, number of total indels in the flanking read with respect to the reference sequence, number of substitutions in the flanking-read repeat with respect to the repeat in the reference sequence, number of insertions in the flanking-read repeat with respect to the repeat in the reference sequence, number of total indels in the flanking-read repeat with respect to the repeat in the reference sequence, number of substitutions in the flanking-read flanking bases with respect to the flanking bases in the reference sequence, number of insertions in the flanking-read flanking bases with respect to the flanking bases in the reference sequence, number of total indels in the flanking-read flanking bases with respect to the flanking bases in the reference sequence, average base quality score of the flanking read, and mapping quality score. In certain versions, each of the plurality of bins encompasses a different value or plurality of values for a sequence attribute selected from the group consisting of repeat length, repeat unit size, and average base quality score of the flanking read. In other certain versions, each of the plurality of bins encompasses a different value or plurality of values for each of repeat length, repeat unit size, and average base quality score of the flanking read.

In some versions, obtaining the sequence-read mapping comprises mapping the sequence reads from the subject polynucleotide sequence to the reference sequence. In some versions, obtaining the sequence-read mapping comprises mapping the sequence reads from the subject polynucleotide sequence to the reference sequence and then locally realigning the aligned sequence reads around indel-containing regions. In some versions, obtaining the sequence-read mapping comprises sequencing the subject polynucleotide sequence to obtain the sequence reads and mapping the sequence reads to the reference sequence.

Another version of the invention comprises a processor. The processor is configured to obtain a sequence-read mapping, wherein the sequence-read mapping comprises sequence reads from a subject polynucleotide sequence mapped to a reference sequence. The processor is also configured to select flanking reads from the sequence reads, wherein each flanking read spans a repeat in the reference sequence in addition to one or more flanking bases on each of two ends of the repeat, and wherein the selecting the flanking reads from the sequence reads results in a flanking-read mapping comprising the repeat and the flanking reads that map thereto. The processor is also configured to extract a sequence attribute from the flanking-read mapping. The processor is also configured to associate the extracted sequence attribute with a genotyping error rate. The processor is also configured to calculate a genotype probability for each flanking read from the genotyping error rate. The processor is also configured to assign a genotype to the subject polynucleotide sequence based on the genotype probabilities calculated for the flanking reads, wherein the genotype comprises a characteristic of a most probable of the flanking reads. The genotype may comprise a repeat length.

In some versions, the processor is configured to extract a sequence attribute selected from the group consisting of repeat length, repeat unit size, repeat unit sequence, repeat purity, number of flanking-read flanking bases on each end of the flanking read, number of exact matches between the flanking-read flanking bases and the flanking bases on the reference sequence, flanking-read length, flanking-base sequence, number of flanking sequences mapped per repeat, number of substitutions in the flanking read with respect to the reference sequence, number of insertions in the flanking read with respect to the reference sequence, number of total indels in the flanking read with respect to the reference sequence, number of substitutions in the flanking-read repeat with respect to the repeat in the reference sequence, number of insertions in the flanking-read repeat with respect to the repeat in the reference sequence, number of total indels in the flanking-read repeat with respect to the repeat in the reference sequence, number of substitutions in the flanking-read flanking bases with respect to the flanking bases in the reference sequence, number of insertions in the flanking-read flanking bases with respect to the flanking bases in the reference sequence, number of total indels in the flanking-read flanking bases with respect to the flanking bases in the reference sequence, average base quality score of the flanking read, and mapping quality score.

In some versions, the processor is configured to extract a sequence attribute selected from the group consisting of repeat length, repeat unit size, and average base quality score of the flanking read.

In some versions, the processor being configured to associate the sequence attribute of the repeat with the genotyping error rate comprises being configured to match the sequence attribute with one of a plurality of bins of partitioned sequence attribute values with known, corresponding genotyping error rates. Each of the plurality of bins may encompass a different value or plurality of values for a sequence attribute selected from the group consisting of repeat length, repeat unit size, repeat unit sequence, repeat purity, number of flanking-read flanking bases on each end of the flanking read, number of exact matches between the flanking-read flanking bases and the flanking bases on the reference sequence, flanking-read length, flanking-base sequence, number of flanking sequences mapped per repeat, number of substitutions in the flanking read with respect to the reference sequence, number of insertions in the flanking read with respect to the reference sequence, number of total indels in the flanking read with respect to the reference sequence, number of substitutions in the flanking-read repeat with respect to the repeat in the reference sequence, number of insertions in the flanking-read repeat with respect to the repeat in the reference sequence, number of total indels in the flanking-read repeat with respect to the repeat in the reference sequence, number of substitutions in the flanking-read flanking bases with respect to the flanking bases in the reference sequence, number of insertions in the flanking-read flanking bases with respect to the flanking bases in the reference sequence, number of total indels in the flanking-read flanking bases with respect to the flanking bases in the reference sequence, average base quality score of the flanking read, and mapping quality score. More specifically, each of the plurality of bins may encompass a different value or plurality of values for a sequence attribute selected from the group consisting of repeat length, repeat unit size, and average base quality score of the flanking read. In some versions, each of the plurality of bins may encompass a different value or plurality of values for each of repeat length, repeat unit size, and average base quality score of the flanking read.

The present invention preferably uses BAM formats for inputting high-throughput sequencing data and VCF and other formats to output genotypes. The present invention may be used with a variety of multi-core processors.

The present invention is advantageous in that it can identify mononucleotide repeats, assign genotypes to a significantly higher percentage of repeat sequences, and maximize correctly mapped reads while minimizing incorrectly mapped reads. The invention offers advantages in optimizing read mapping for microsatellite repeat genotyping, identifying genotyping errors through evaluation of genotype consistency with the Mendelian inheritance theory, and uses common formats to ensure compatibility with other variant callers and existing genotyping pipelines. The invention can improve studies of genome stability and neurodegenerative diseases.

The objects and advantages of the invention will appear more fully from the following detailed description of the preferred embodiment of the invention made in conjunction with the accompanying drawings.

BRIEF DESCRIPTION OF THE DRAWINGS

FIGS. 8A and B show that variability is positively correlated with purity (FIG. 8A) and negatively correlated with unit size (FIG. 8B). Correlations were made using genotypes of pure repeats (2mers to 5mers) that were derived from genomes sequenced with a read length of at least 75 bases. Data points were plotted at each reference length bin interval that contained at least 25 repeats. The values plotted are the mean completeness or concordance values where each data point reflects an average for repeats with a reference length within 2 bases of the plotted repeat length.

FIGS. 10A-D depict the number of repeats as a function of difference in allele length for repeats with 2mer repeat units (FIG. 10A), 3mer repeat units (FIG. 10B), 4mer repeat units (FIG. 10C), and 5mer repeat units (FIG. 10D). Changes in repeat length typically occur in the form of insertions and deletions of whole repeated units. The plotted dataset consisted of repeats that were at least 90% pure, with a minimum reference repeat length of 13, 20, 23, and 27 bases for 2mers, 3mers, 4mers, and 5mers, respectively. Genotypes were determined if there were at least two scorable reads and a read was scored if it spanned the repeat region with 3 or more matching flank bases on either side of the repeat.

FIG. 11A shows the frequency of all repeats 80% pure or greater.

DETAILED DESCRIPTION OF THE INVENTION

Figure 1:
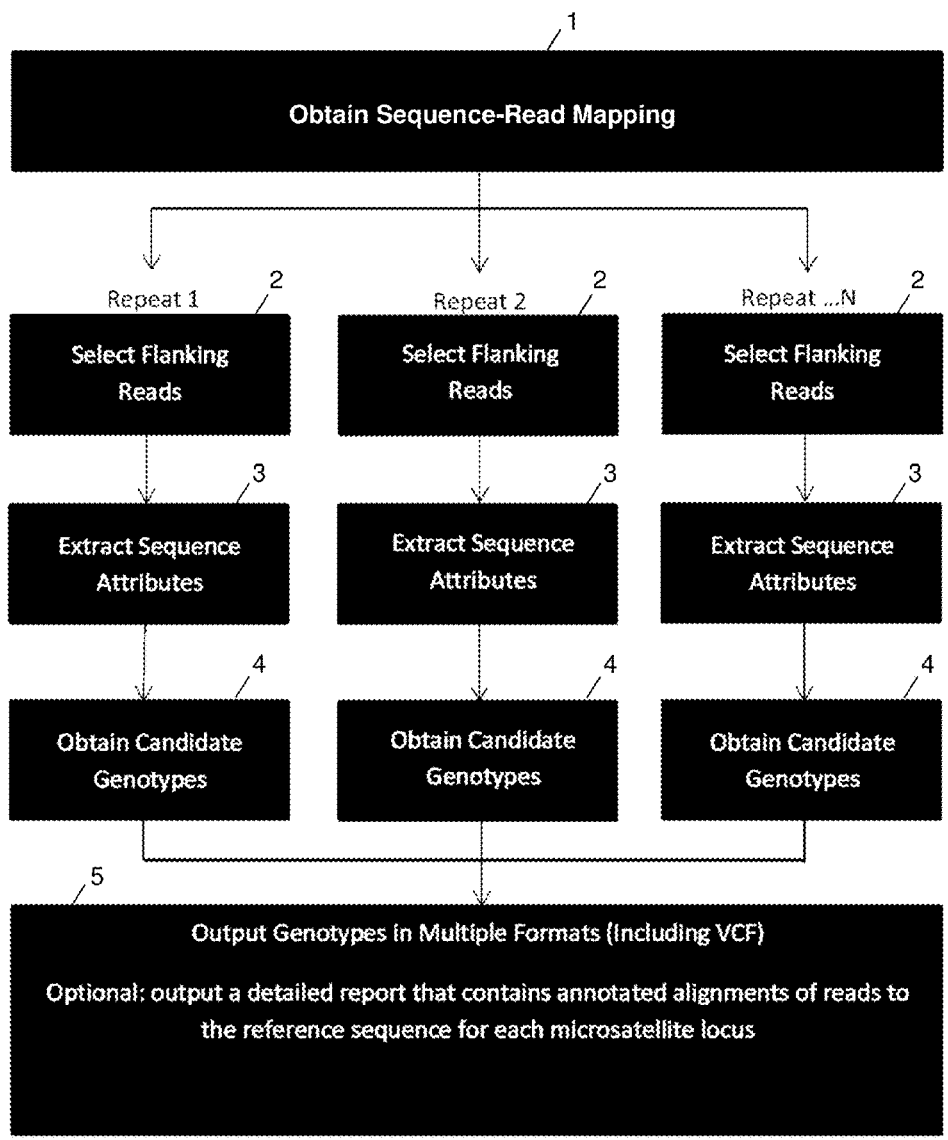
FIG. 1 depicts a schematic overview of an exemplary method of the present invention.

FIG. 1 depicts a schematic overview of an exemplary method of the present invention. In a first step 1, a sequence-read mapping is obtained. The sequence-read mapping comprises one or more sequence reads from a subject polynucleotide sequence that are mapped (aligned) to a reference sequence. In a second step 2, flanking reads are obtained. Flanking reads comprise the sequence reads that overlap at least an entire repeat on the reference sequence in the sequence-read mapping. In a third step 3, sequence attributes are extracted. The extracted sequence attributes pertain to characteristics of the flanking reads, the repeats to which the flanking reads map, or the alignment of the flanking reads to the repeats are extracted. In a fourth step 4, candidate genotypes for the subject polynucleotide are obtained (assigned). The assignment is preferably based at least in part on previously determined error rates associated with sequence attributes that are similar to the extracted sequence attributes. In preferred versions of the invention, the steps of selecting flanking reads, extracting sequence attributes, and obtaining candidate genotypes are performed for each repeat in the reference sequence. In a fifth step, the assigned genotypes for the subject polynucleotide are output for downstream use.

Figure 2:
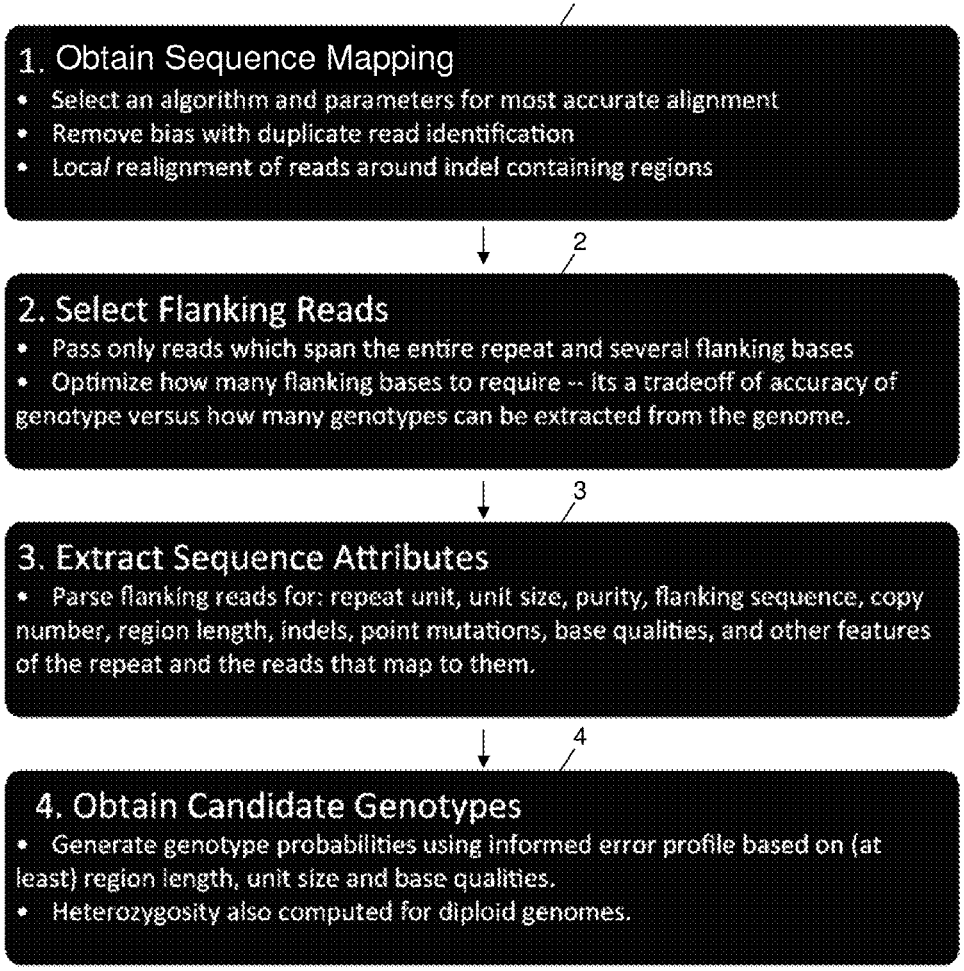
FIG. 2 outlines exemplary sub-steps for the steps shown in FIG. 1.

FIG. 2 outlines optional sub-steps for the first through fourth steps shown in FIG. 1. For example, obtaining the sequence-read mapping 1 may comprise selecting an algorithm and parameters for an accurate alignment, removing duplicate sequence reads from the resulting alignment, and locally realigning the sequence reads around indel-containing regions. Selecting the flanking reads 2 may be optimized to maximize genotype accuracy along with the number of genotypes that can be assigned to a particular genome. Extracting sequence attributes 3 may comprise parsing the flanking reads for such sequence attributes as repeat length, repeat unit size, flanking-read base quality, sequence of repeat unit, repeat purity, sequence of flanking bases, number of flanking bases, presence or number of indels within the repeat, and presence or number of point mutations within the repeat. Obtaining the candidate genotypes 4 may comprise generating genotype probabilities using prior-defined error profiles based on particular sequence attributes. Heterozygosity may also be computed for diploid genomes.

The term "sequence" is used herein to refer to a linear string of nucleotide bases in a nucleic acid (polynucleotide) such as DNA and RNA. The term may refer to the actual bases in the nucleic acid itself, or a representation of the string of nucleotide bases in a text- or digital-based format, such as FASTA, Binary Alignment/Map (BAM), Sequence Alignment/Map (SAM), and Variant Call Format (VCF) formats. In some formats, such as FASTA, the string of nucleotide bases in a particular sequence is explicitly presented. In other formats, the string of nucleotide bases in a particular sequence is implied by showing nucleotide changes relative to a second sequence. Common abbreviations that represent the constituent bases in a DNA sequence are as follows: A=adenine; C=cytosine; G=guanine; T=thymine; R=G or A (purine); Y=T or C (pyrimidine); K=G or T (keto); M=A or C (amino); S=G or C (strong bonds); W=A or T (weak bonds); B=G, T, or C (all but A); D=G, A, or T (all but C); H=A, C, or T (all but G); V=G, C, or A (all but T); and N=A, G, C, or T (any). These abbreviations are also commonly used for RNA, except with U (uracil) replacing T (thymine).

As used herein, "repeat," used in reference to a portion of sequence, refers to two or more contiguous, approximate copies of a pattern of polynucleotides. Examples of repeats are the polynucleotide structures known in the art as "microsatellites," "microsatellite repeats," "simple sequence repeats (SSRs)," or "short tandem repeats (STRs)." The term "repeat unit" refers to the cluster of bases that is copied within a repeat. The term "repeat unit size" refers to the number of bases in the repeat unit. The term "repeat unit sequence" refers to the sequence of a repeat unit. The repeat unit in any given repeat may comprise 1 to 10 or more bases and may occur from 2 to 100 or more times within the repeat. Repeats with repeat units of 2 to 6 bases are common in genomic DNA.

A repeat is flanked on both the upstream (5') side and the downstream (3') side by flanking bases, which disrupt and effectively end the repetition of the repeat units on either side of the repeat. The term "repeat length" refers to the number of bases in a repeat between the flanking bases. Repeat lengths can range from 2 to 100 or more bases. Repeat lengths of less than about 60 bases, such as from about 20 to 60 bases, are common. See, e.g., Example 1 and FIGS. 11A and B.

A pure repeat is a repeat in which copies of the repeating unit occur without interruption. An impure repeat is a repeat in which the copies of the repeating units are interrupted. Various types of interruption can include an insertion of a base within a repeat unit or between repeat units, a deletion of a base from a repeat unit, or a substitution a base in a repeat unit. The degree to which a repeat is pure is referred to as its "purity." A repeat's purity can be expressed as a percent purity. Percent purity can be determined by subtracting the number of interruptions in the pattern of repeating units within a given repeat from the repeat length, and dividing the difference by the repeat length. See e.g., Example 1 and FIG. 8A.

As outlined above, a repeat can be characterized by the repeat length, the repeat unit size, the sequence of the repeat unit, repeat purity, or other characteristics. These characteristics can be determined with such programs as the Tandem Repeats Finder (TRF) described by Benson.

The reference sequence may comprise any known sequence that includes a repeat. The reference sequence may have any length, provided it can accommodate a repeat. For example, the reference sequence may have a size ranging from 4 to about a trillion or more base pairs. In preferred versions of the invention, the reference sequence represents an individual's genome or portion thereof, or a single consensus of the genomes (or respective portions thereof) from a collection of individuals in a given population. The reference sequence is preferably used as a baseline for genotyping non-reference sequences. Repeats in a reference sequence can be identified by a number of methods. One method, outlined in Example 1, includes identifying repeats with such programs as Tandem Repeats Finder (TRF) (Benson). Other methods are known in the art.

The sequence read may comprise any sequence that is capable of mapping to a reference sequence. The sequence read may have any length, provided it can map to a reference sequence. Exemplary sequence read lengths may range from 4 to about 5,000 bp or more. In certain versions of the invention, such as those directed for use in some next-generation sequencing methods, the sequence read lengths may range from 4 to about 500 bp, including ranges of from about 10 to about 400 bp, or about 30 to about 300 bp.

The sequence reads in the sequence-read mapping may be obtained from sequencing a polynucleotide. Each sequence read in such a case is the sequence that results from a single run of a sequencing reaction. Such sequence reads are referred to herein as "sequencing reads." The sequenced polynucleotide may comprise a genome or any portion thereof, including coding regions, non-coding regions, or isolated genomic fragments. The sequenced polynucleotide may alternatively comprise a synthetic polynucleotide. Any method of sequencing a polynucleotide known or developed in the future can be used with the present invention. Exemplary methods include Maxam-Gilbert sequencing, chain-termination (Sanger) sequencing, and the many types of "next-generation" sequencing methods. Examples of next-generation sequencing methods include massively parallel signature sequencing (MPSS), polony sequencing, pyrosequencing, sequencing by ligation, ion torrent semiconductor sequencing, and DNA nanoball sequencing, heliscope single molecule sequencing, and single molecule read time (SMRT) sequencing. Examples of commercialized versions of these or other next-generation sequencing methods include the SOLiD® Next Generation Sequencing platform by Life Technologies (Carlsbad, Calif.), the 454 Sequencing™ platform from 454 Life Sciences (Roche Applied Science, Basel, Switzerland), and the sequencing by synthesis sequencing platform by Illumina® (San Diego, Calif.). The invention is particularly suited for genotyping with the shorter sequencing reads that result from the next-generation sequencing methods. While the sequence reads are preferably derived from the sequencing of an actual polynucleotide, synthetic sequence reads generated in silico can also be used in the present invention.

One aspect of the invention comprises obtaining a sequence-read mapping that has one or more sequence reads mapped to a reference sequence. The sequence-read mapping can be obtained by aligning the sequence reads to the reference sequence using any of a number of mapping algorithms known in the art. Exemplary mapping algorithms include Bowtie2 (Langmead et al.), BWA (Li and Durbin 2010), Novoalign (Novocraft Technologies), Stampy (Lunter et al.) and SMALT (Wellcome Trust Sanger Institute). See Example 2. The sequence-read mapping can also be obtained by incorporating a pre-generated sequence-read mapping into a genotyping module 10, as described in further detail below.

A suitable sequence-read mapping for use in the present invention comprises at least one sequence read mapped to at least one repeat on the reference sequence. It is preferred for accuracy in genotyping, however, that the sequence-read mapping comprises a plurality of reads per repeat. Preferred coverage of the repeat (number of sequence reads mapped per repeat) comprises at least about 2× coverage, at least about 5× coverage, at least about 10× coverage, at least about 15× coverage, at least about 20× coverage, or more. Such coverage is preferably obtained for at least one repeat in the reference sequence. Such coverage is preferably obtained for more than one repeat in the reference sequence, including at least about 25% of the repeats in the reference sequence, at least about 50% of the repeats in the reference sequence, or at least about 75% of the repeats in the reference sequence.

An advantage of the present invention is that it can make genotyping calls with minimal coverage data. Therefore, in versions of the invention, the sequence-read mapping can comprise coverage of the repeat less than about 20× coverage, less than about 15× coverage, less than about 10× coverage, and less than about 5× coverage, such as about 3× or about 2× coverage. Such coverage may occur for at least one repeat in the reference sequence. Such coverage may also occur for more than one repeat in the reference sequence, including at least about 25% of the repeats in the reference sequence, at least about 50% of the repeats in the reference sequence, or at least about 75% of the repeats in the reference sequence.

Several steps can be performed on the initial sequence-read mapping obtained from the mapping algorithm to generate a more accurate sequence-read mapping, thereby facilitating more accurate genotyping. One step includes marking and/or eliminating duplicate sequence reads. Duplicate sequence reads can originate from DNA preparation methods and can causes biases that skew the genotyping results. The duplicate reads in a sequence-read mapping can be marked using the Picard program available from the Broad Institute (Cambridge Mass.).

Another step that can be performed on the initial sequence-read mapping is local realignment. Local realignment locally realigns reads such that the number of mismatching bases is minimized across all the reads. A large percent of regions requiring local realignment are due to the presence of an insertion or deletion (indels) in a subject sequence with respect to a reference sequence. Such alignment artifacts result in many bases mismatching the reference near the misalignment, which are easily mistaken as single nucleotide polymorphisms (SNPs). Moreover, since read mapping algorithms operate on each read independently, they fail to place reads on the reference genome such that mismatches are minimized across all reads. Consequently, even when some reads are correctly mapped with indels, reads covering the indel near just the start or end of the read are often incorrectly mapped with respect the true indel, also requiring realignment. Local realignment transforms regions with misalignments due to indels into clean reads containing a consensus indel suitable for standard variant discovery approaches. A preferred tool for performing local realignment is the GATK IndelRealigner tool available from the Broad Institute (Cambridge Mass.).

An additional aspect of the invention comprises selecting flanking reads from the sequence reads in the sequence-read mapping. The term "flanking read" is used to refer to a sequence read that spans an entire repeat in the reference sequence. In preferred versions of the invention, the flanking read spans a repeat in the reference sequence in addition to one or more flanking bases on each of the two ends of the repeat. In various versions of the invention, the flanking reads may comprise sequence reads that span at least one flanking base on each of the two ends of the repeat, at least two flanking bases on each of the two ends of the repeat, at least three flanking bases on each of the two ends of the repeat, at least four flanking bases on each of the two ends of the repeat, or at least five flanking bases on each of the two ends of the repeat. In preferred versions of the invention, the flanking reads comprise perfect matches for at least at least one flanking base on each of the two ends of the repeat, perfect matches for at least two flanking bases on each of the two ends of the repeat, perfect matches for at least three flanking bases on each of the two ends of the repeat, perfect matches for at least four flanking bases on each of the two ends of the repeat, or perfect matches for at least five flanking bases on each of the two ends of the repeat. The step of selecting flanking reads may be performed separately for any number of the repeats in the reference sequence. Selecting the flanking reads effectively generates a flanking-read mapping, which comprises the flanking reads that map to a single repeat as well as the repeat itself. Each flanking read comprises either an exact or an inexact copy of the repeat and the flanking bases spanned by the flanking read. The term "flanking-read repeat" refers to the copy of the repeat represented in the flanking read. The term "flanking-read flanking base" refers to the copy of any flanking base represented in the flanking read.

An additional aspect of the invention comprises extracting sequence attributes from the flanking-read mapping. As used herein, "sequence attribute" refers to any characteristic of a flanking read, a repeat and/or flanking bases on a reference sequence to which the flanking read maps, and/or an alignment of the flanking read to the reference sequence. The step of extracting sequence attributes may be performed separately for any number of the repeats in the reference sequence and each flanking read mapping thereto. Exemplary types of sequence attributes include repeat length, repeat unit size, repeat unit sequence, repeat purity, number of flanking-read flanking bases on each end of the flanking read, number of exact matches between the flanking-read flanking bases and the flanking bases on the reference sequence, flanking-read length, flanking-base sequence, number of flanking sequences mapped per repeat, number of substitutions in the flanking read with respect to the reference sequence, number of insertions in the flanking read with respect to the reference sequence, number of total indels in the flanking read with respect to the reference sequence, number of substitutions in the flanking-read repeat with respect to the repeat in the reference sequence, number of insertions in the flanking-read repeat with respect to the repeat in the reference sequence, number of total indels in the flanking-read repeat with respect to the repeat in the reference sequence, number of substitutions in the flanking-read flanking bases with respect to the flanking bases in the reference sequence, number of insertions in the flanking-read flanking bases with respect to the flanking bases in the reference sequence, number of total indels in the flanking-read flanking bases with respect to the flanking bases in the reference sequence, average base quality score of the flanking read, and mapping quality score.

Methods for determining and, therefore, extracting such sequence attributes as repeat length, repeat unit size, repeat unit sequence, repeat purity, number of flanking-read flanking bases on each end of the flanking read, number of exact matches between the flanking-read flanking bases and the flanking bases on the reference sequence, flanking-read length, flanking-base sequence, number of flanking sequences mapped per repeat, number of substitutions in the flanking read with respect to the reference sequence, number of insertions in the flanking read with respect to the reference sequence, number of total indels in the flanking read with respect to the reference sequence, number of substitutions in the flanking-read repeat with respect to the repeat in the reference sequence, number of insertions in the flanking-read repeat with respect to the repeat in the reference sequence, number of total indels in the flanking-read repeat with respect to the repeat in the reference sequence, number of substitutions in the flanking-read flanking bases with respect to the flanking bases in the reference sequence, number of insertions in the flanking-read flanking bases with respect to the flanking bases in the reference sequence, and number of total indels in the flanking-read flanking bases with respect to the flanking bases in the reference sequence are apparent from the foregoing description.

The base quality score of a given base in a sequencing read is the probability that the base is called incorrectly by a sequencer. Each base in a read is assigned a quality score by a Phred-like algorithm (Ewing and Hillier et al., Ewing and Green), similar to that originally developed for Sanger sequencing experiments. The quality score of a given base, Q, is defined by the equation:

$$Q = -10 \log_{10}(e)$$

where e is the estimated probability of the base call being wrong. A higher quality score indicates a smaller probability of error. A quality score of 20 (Q20) represents an error rate of 1 in 100, with a corresponding call accuracy of 99%. A quality score of 30 (Q30) represents an error rate of 1 in 1000, with a corresponding call accuracy of 99.9%. An exemplary tool for determining base quality scores is the BaseRecalibrator tool available from the Broad Institute. Other tools are known in the art. The average base quality score of the flanking read can be calculated by averaging the quality scores of each of the bases in the flanking read.

Mapping quality scores indicate the confidence that a particular sequence read is accurately placed with respect to a reference sequence. A method for determining mapping quality scores are provided by Li et al. 2008. Mapping quality scores are provided by the mapping algorithms described herein after mapping a sequence read to a reference sequence.

A further aspect of the invention comprises associating the extracted sequence attributes with a genotyping error rate. The term "error rate" refers to the rate at which a genotype is called in error. Associating the extracted sequence attributes with a genotyping error rate is preferably performed by using the extracted sequence attributes to identify empirically derived genotyping error rates associated with previous genotyping using sequence reads and reference sequences having similar sequence attributes. The term "genotyping" is used herein to refer to making a determination whether a particular characteristic of a sequence read, such as a flanking read, represents either a true characteristic of a subject sequence from which the sequence read is derived or an artifact. Various artifacts that may appear in a sequence read may comprise sequencing artifacts, e.g., artifactual indels or substitutions appearing in the sequence read; mapping artifacts, e.g., matching a sequence read to an incorrect repeat or misaligning a sequence read with respect to a repeat on which it is correctly matched; or others. Accordingly, the error rate can account for various types of factors that may affect genotyping, including sequencing error, e.g., error resulting from the sequencing process; computer error, e.g., error resulting from mapping, etc., and biological factors, e.g., the propensity of a certain type of repeat to mutate upon replication. In the case of genotyping repeats, the characteristic that is assigned in genotyping is preferably the repeat length, although other characteristics such as SNPs, indels, etc., can also be assigned.

Different error rates can be associated with the extracted sequence attributes for each repeat or each flanking read, depending on the particular extracted sequence attribute. Such versions of the invention are distinguished from versions in which a constant error rate is employed for each and every repeat and sequence read. See Example 2.

The extracted sequence attributes can be associated with the known genotyping error rates by partitioning the sequence attributes from prior genotyping in bins along with the corresponding known error rates, matching the extracted sequence attributes with a bin encompassing the same attributes, and assigning the genotyping error rate from the matched bin to the extracted sequence attributes. In order for the matching to occur, the partitioned sequence attributes should be of the same type as the extracted sequence attributes. The partitioned sequence attributes can therefore be selected from repeat length, repeat unit size, repeat unit sequence, repeat purity, number of flanking-read flanking bases on each end of the flanking read, number of exact matches between the flanking-read flanking bases and the flanking bases on the reference sequence, flanking-read length, flanking-base sequence, number of flanking sequences mapped per repeat, number of substitutions in the flanking read with respect to the reference sequence, number of insertions in the flanking read with respect to the reference sequence, number of total indels in the flanking read with respect to the reference sequence, number of substitutions in the flanking-read repeat with respect to the repeat in the reference sequence, number of insertions in the flanking-read repeat with respect to the repeat in the reference sequence, number of total indels in the flanking-read repeat with respect to the repeat in the reference sequence, number of substitutions in the flanking-read flanking bases with respect to the flanking bases in the reference sequence, number of insertions in the flanking-read flanking bases with respect to the flanking bases in the reference sequence, number of total indels in the flanking-read flanking bases with respect to the flanking bases in the reference sequence, average base quality score of the flanking read, and mapping quality score, among others.

For the partitioning of each sequence attribute type, each bin can encompass a single sequence attribute value or a plurality of sequence attribute values for that type. The plurality of sequence attribute values can comprise a range of values or any other grouping of values. For example, if the sequence attribute type is a quantitative variable, such as average base quality score, each bin can encompass a single sequence attribute value (e.g., a single base quality score) or a range of sequence attribute values (e.g., range of base quality scores). If the sequence attribute type is a qualitative variable, such as repeat unit sequence, each unique repeat unit sequence can be partitioned into its own bin. However, if it is empirically determined that certain repeat unit sequences result in the same genotyping error rate, these repeat unit sequences can be grouped in the same bin. The sequence attribute type can be partitioned according to any suitable number of bins, including 2-10 or more.

The partitioning of bins can be based on a single sequence attribute type or a plurality of sequence attributes types. If the partitioning is based on a single sequence attribute type, each bin can encompass the known error rate corresponding to one or more values for that type of sequence attribute. The bins in such a case comprise a unidimensional error profile. If the partitioning is based on a plurality of sequence attribute types, each bin can encompass the known error rate corresponding to the combination of one or more values for each of the plurality of sequence attributes types contained in the bin. The bins in such a case comprise multidimensional error profile with each dimension representing a different sequence attribute.

Once the extracted sequence attributes are associated with a genotyping error rate, the probability of each flanking read representing a true genotype, rather than an artifact, is calculated. Calculating the genotype probabilities is preferably performed by incorporating the genotyping error rate as a prior in Bayes' rule. Exemplary terms and equations for performing such calculations are described in detail in Example 2. A genotype is then assigned to the subject sequence based on the calculated genotype probabilities. In the preferred version of the invention, the assigned genotype is the most probable genotype. In some versions of the invention, a genotype is assigned only if the most probable genotype has a probability greater than about 50%.

The steps described above can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

Figure 3:
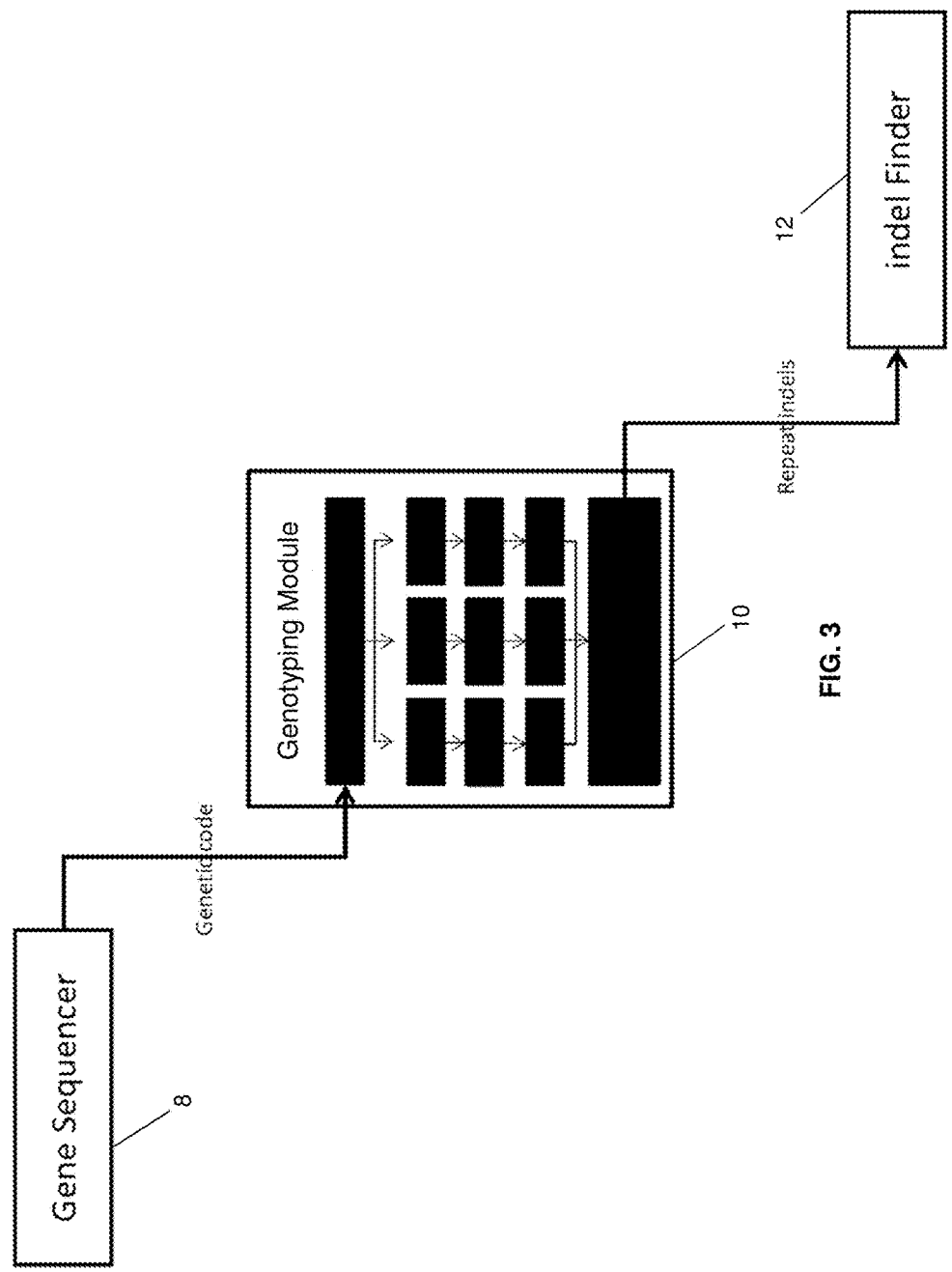
FIG. 3 shows an exemplary system of the present invention comprising a genotyping module 10 configured to import sequence reads from a sequencer 8 and further configured to output genotypes to an external module 12.
Figure 4A:
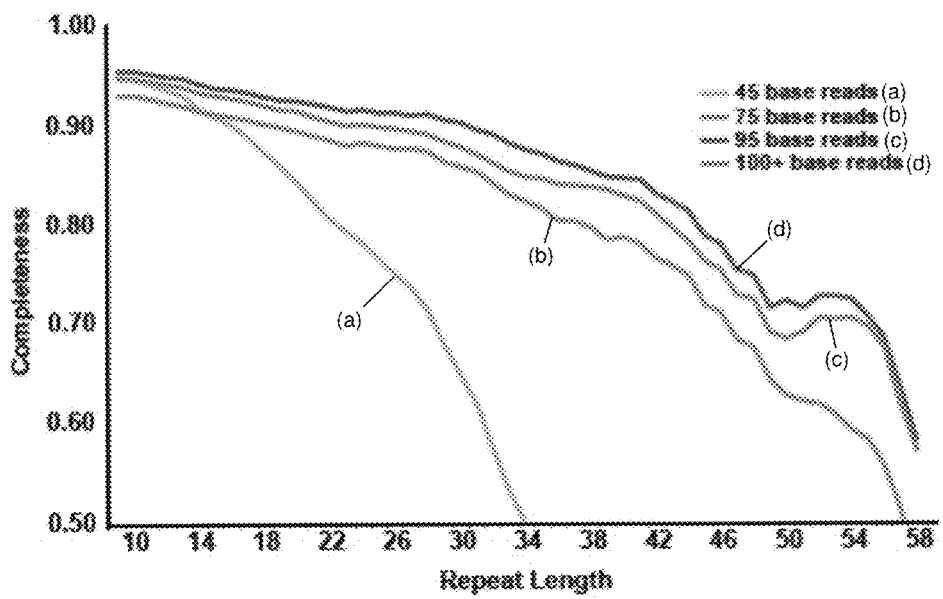
FIGS. 4 and B show completeness (FIG. 4A) and internal concordance (FIG. 4B) of microsatellite repeat genotypes in the *Drosophila* genome as a function of repeat length for various base read lengths. A single matching base on each side of the repeat was required for a read to be scored and two or more scorable reads were required to determine a repeat genotype. The plotted values are the mean completeness or concordance values of repeats that are at least 80% pure and each data point reflects an average for repeats with a reference length within 2 bases of the plotted repeat length.
Figure 4B:
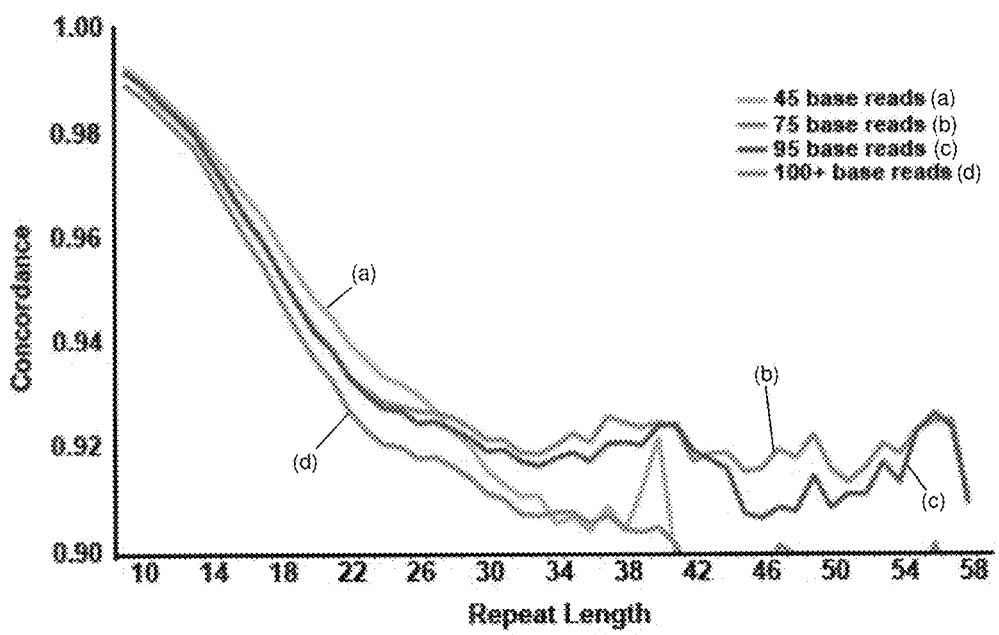

In one version of the invention, shown in FIG. 3, the various steps described above are implemented on a genotyping module 10 comprising a processor configured to carry out the steps. The steps carried out on the genotyping module 10 may include the steps of obtaining the sequence-read mapping, selecting the flanking reads, extracting sequence attributes, and obtaining candidate genotypes, as depicted in FIGS. 1 and 2. The step of obtaining the sequence-read mapping performed by the genotyping module 10 may include a step of mapping the sequence reads to the reference sequence, or, alternatively, may include incorporating a pre-formed sequence-read mapping therein. The genotyping module 10 may also include the steps of removing duplicate reads and/or locally realigning the reads. The step of obtaining candidate genotypes may comprise associating the extracted sequence attributes with a genotyping error rate, calculating genotype probabilities for each flanking read from the genotyping error rate, and assigning a genotype to a subject polynucleotide sequence based on the genotype probabilities for each flanking read, as described above. The error profiles (i.e., binned sequence attributes from prior genotyping) are stored in a database. The database is either contained within the genotyping module 10 itself or is stored on a separate module that is accessible by the genotyping module 10.

As shown in FIG. 3, the genotyping module 3 is configured to incorporate sequence reads generated from sequencing a subject polynucleotide sequence with a sequencer 8. The sequence reads are incorporated either as sequence reads unmapped to a reference sequence or as sequence reads mapped to a reference sequence. The genotyping module 3 then genotypes the subject polynucleotide sequence with the sequence reads. The genotyping module 3 can then output the genotypes in any of a number of formats (VCF, alignments, etc.; see step 5 in FIG. 2) to an external module 12. Any of a number of downstream applications can then be performed, such as diagnosing disease or other applications as described elsewhere herein.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Example 1—Analysis of Microsatellite Variation in *Drosophila melanogaster* with Population-Scale Genome Sequencing Summary Genome sequencing technologies promise to revolutionize the understanding of genetics, evolution, and disease by making it feasible to survey a broad spectrum of sequence variation on a population scale. However, this potential can only be realized to the extent that methods for extracting and interpreting distinct forms of variation can be established. The error profiles and read length limitations of early versions of next-generation sequencing technologies rendered them ineffective for some sequence variant types, particularly microsatellites and other tandem repeats, and fostered the general misconception that such variants are inherently inaccessible to these platforms. At the same time, tandem repeats have emerged as important sources of functional variation. Tandem repeats are often located in and around genes, and frequent mutations in their lengths exert quantitative effects on gene function and phenotype, rapidly degrading linkage disequilibrium between markers and traits. Sensitive identification of these variants in large-scale next-generation sequencing efforts will enable more comprehensive association studies capable of revealing previously invisible associations. The example below presents a population-scale analysis of microsatellite repeats using whole-genome data from 158 inbred isolates from the *Drosophila* Genetics Reference Panel, a collection of over 200 extensively phenotypically characterized isolates from a single natural population, to uncover processes underlying repeat mutation and to enable associations with behavioral, morphological, and life-history traits. Analysis of repeat variation from next-generation sequence data will also enhance studies of genome stability and neurodegenerative diseases.

Background

Advances in genome technology are accelerating the understanding of the genetic basis for common traits and diseases. Large-scale efforts such as the HapMap Project have produced an initial catalog of genetic variants, primarily single nucleotide polymorphisms (SNPs), that has facilitated association studies with phenotypes (Altshuyler et al.). The advent of accurate and cost-effective next-generation sequencing methods has now enabled the production of even more detailed maps of genetic variation. The 1000 Genomes Project and the Cancer Genome Atlas Project, for example, promise to illuminate genetic population structure and the genetic contribution to trait and disease phenotypes (Durbin et al.; TCGA 2008 *Nature*). However, an issue of missing heritability has been identified in many association studies, even for strongly heritable traits such as height (Lango et al). The paucity of identified genetic determinants in genome-wide association studies may be partially explained by their reliance on high-frequency SNPs. At least in part due to technical limitations, the potential contributions of other forms of variation remains less fully explored (Manolio et al.).

Although much-used in the heyday of genetic linkage studies, polymorphic short tandem repeats, or microsatellites, were largely rendered obsolete as genetic markers by the advent of genotyping microarrays, and are not broadly employed in genome-wide association studies (Hannon). However, tandem repeats continue to be broadly utilized as markers for genome instability and prognostic indicators for some forms of cancer (Lynch et al., Reuschenback et al.). The roles of tandem repeats as causative agents of disease has been defined for a wide range of neurological and morphological disorders (Lopez et al., Orr, Albrecht et al. 2005). Furthermore, coding microsatellites are enriched in transcription factors and other regulatory proteins, where changes in repeat length exert incremental impacts on gene function (Gerber et al., Albrecht et al. 2004, Verstrepen et al.). Variations in the lengths of noncoding repeats in the promoters of genes have been shown to quantitatively affect transcription and can facilitate transcriptional plasticity (Vinces et al.). Emerging evidence implicates coding and noncoding microsatellites as important sources of common genetic variation in morphological and behavioral traits in numerous species, including bacteria, yeast, flies, mice, dogs, and humans (Gemayel et al.).

Despite the functional importance and unparalleled phylogenetic signal provided by tandem repeat variation, technical challenges have prevented its inclusion in the recent spate of "comprehensive" genomic variation analyses (Manolio et al., Melver et al.). Genotyping microsatellite repeats using next-generation sequencing is challenging for several reasons. At minimum, an individual read must span the entire repeat plus some flanking non-repetitive sequence for reliable local alignment and allele length determination. Furthermore, since repeats are abundant in most genomes, substantial additional unique sequence must be present in either the same read, or more commonly within its paired-end mate, to correctly map a repeat-containing read to the reference genome. The error spectra of some next-generation platforms further complicate the reliable ascertainment of repeat allele lengths. These issues extend beyond the well-known problems with mononucleotide repeats for the Roche 454 platform (454 Life Sciences, Roche, Branford, Conn.), affecting essentially all repeat types and platforms to some extent (Albers et al.). However, the advent of paired-end sequencing and increasingly longer read lengths are enabling more sensitive and accurate detection of structural variants and other problematic sequence variations (Albers et al., Bashir et al., Mills and Walter et al. 2011).

The present example introduces a method to accurately genotype microsatellite repeats from next-generation sequencing data and presents a population-scale analysis of microsatellite repeats using assemblies of whole-genome Illumina (Illumina Inc., San Diego, Calif.) data from 158 inbred isolates from the Drosophila Genetics Reference Panel (Mackay et al.). These lines are a subset of nearly 200 extensively phenotypically characterized isolates from a single natural population from the Raleigh, N.C., USA area. The example shows that nearly a third of the 390,873 examined microsatellites are variable within this population, and confirmed a sample of these by Sanger sequencing. Next, the example shows that these polymorphic repeats generally conform to accepted models for repeat evolution in that repeat variation is predominantly in the form of insertions or deletions of whole repeat units, and polymorphism is correlated with repeat length and purity (i.e. fewer interruptions in the repeat sequence). These data help illuminate the processes underlying repeat mutation and will be instrumental in determining the contribution of repeats to quantitative variation in behavioral, morphological, and life-history traits.

Methods

Identifying Microsatellite Repeats from the Drosophila Reference

Microsatellites were identified in the Drosophila melanogaster reference genome (release 5.13) using TRF v4.04 (Benson) using parameters "2 5 5 80 10 14 5," and filtered to remove redundant hits. Microsatellites within or adjacent to regions that preclude unique mapping were excluded, including larger repetitive elements and heterochromatin.

Transposons and other repetitive elements that confound short read mapping were identified using RepeatMasker (version 20071705; library release 20061006; -s setting). RepeatMasker results were filtered to remove all "Simple_repeat" and "Low_complexity" hits, and TRF-identified microsatellites occurring within 20 bases with of a RepeatMasker interval were removed. This reduced the microsatellite set from 634,892 regions to 556,361. A disproportionate number of the removed microsatellites were in heterochromatin and unscaffolded contigs (which are also mostly heterochromatin). The heterochromatic regions were therefore from analysis. The final set included 390,873 microsatellites.

Mapping Illumina Whole-Genome from the DGRP Lines

Methods for library preparation and sequencing are described elsewhere (Mackay et al.). For the present study, all of the sequences for all 158 lines were mapped to the Dmel 5.13 reference genome using BWA (version 0.5.8c) with the "-n 5 -o 1 -e 3 -1 25" parameters (Li and Durbin 2009).

Microsatellite Genotype Inference

For each TRF-identified microsatellite, genotypes were scored by allele length, or the number of sequenced bases within a read separating the non-repetitive flanking boundaries aligned to the reference, irrespective of intervening alignment gaps. This approach ensures that insertions or deletions aligned to different portions of the repeat region in different reads are not scored as distinct alleles.

Correlations to Length, Unit Size, and Purity

To examine the relationships between unit size or purity and variability, genotypes of microsatellites of given unit sizes and purity values were analyzed to determine the number of unique alleles found within the DGRP dataset. The TRF-reported unit size and purity values were used to categorize the microsatellites by unit size or purity, while the most frequently observed allele length in the population was used for repeat length. Repeats were binned by length, and the mean number of distinct alleles for each bin was determined.

Bootstrapping Analysis

To evaluate the significance of allelic bias in 45-base versus 75-base libraries, 1,000 frequency distributions of allele length difference at discordant loci were created using microsatellites randomly sampled from the original set with replacement. For each allele length difference bin, the frequency values from each of these 1,000 randomized sets of repeats were sorted into increasing order and the 2.5th and 97.5th percentiles were plotted.

Exclusion of Residual Heterozygosity

Regions of apparent heterozygosity within individual lines on the basis of heterozygous SNP genotypes were obtained from the DGRP project site (Mackay et al.). Chromosomal arms were excluded from individual lines for concordance measurements if more than 5% of single nucleotide polymorphism sites were scored as heterozygous.

Results

Length Distribution of Repeats in the Drosophila Melanogaster Reference Sequence Sequence read length determines the upper bound of repeat allele lengths that can be reliably determined by DNA sequencing. It is therefore useful to examine the distribution of repeat lengths in the finished D. melanogaster reference genome to estimate the proportion of microsatellite loci expected to be within reach of short read libraries. All perfect and imperfect microsatellite repeats with a unit length of up to five nucleotides from build 5.13 of the D. melanogaster nuclear DNA reference sequence were identified (see Methods above). About 12% of these microsatellites reside within or adjacent to larger repetitive elements, in heterochromatic regions, or in unscaffolded contigs to which reads cannot be uniquely mapped, and were excluded from further consideration (Table 1). Of a total of 390,873 microsatellite repeats satisfying minimum length and purity specifications, 92,047 (24%) were mononucleotides, 58,153 (15%) were dinucleotides, 95,234 (24%) were trinucleotides, 78,264 (20%) were tetranucleotides, and 67,175 (17%) were pentanucleotides. The median repeat length was 11 bases (range 7-651), and 90% of repeats were shorter than 23 nucleotides. Over 98% of microsatellites were accessible to the shortest reads employed in the DGRP sequencing libraries (45 bases), while only 165 repeats (0.04%) were beyond the reach of the longest reads (110 bases).

TABLE 1

Number of identified microsatellites and their
association with repetitive elements by chromosome.

| Chromosome | Total microsats | Number (%) in REs[a] |
|---|---|---|
| 2L | 103,467 | 6,444 (6) |
| 2LHet | 1,083 | 837 (77) |
| 2R | 92,291 | 7,306 (8) |
| 2RHet | 10,388 | 7,556 (73) |
| 3L | 114,997 | 7,719 (7) |
| 3LHet | 8,803 | 6,326 (72) |
| 3R | 127,212 | 4,328 (3) |
| 3RHet | 8,414 | 6,351 (75) |
| 4 | 6,603 | 2,064 (31) |
| U | 28,559 | 21,274 (74) |
| X | 131,339 | 7,356 (6) |
| XHet | 813 | 415 (51) |
| YHet | 923 | 555 (60) |

[a]Number (%) of microsatellites within 20 bases of a large repetitive element.

Microsatellite Genotype Determination

The number and specific identities of deleted or inserted repeat units separating two different (or even identical) microsatellite alleles in a population is generally unknowable (Sainudiin et al.). Genotyping tandem repeat variants in reference-mapped reads is therefore fundamentally distinct from calling SNPs or indels in non-repetitive sequence in that there is no sound basis for inferring homology between pairs of aligned repeat units. Therefore, microsatellite genotypes are scored in terms of allele length, or the number of sequenced bases within a read separating the non-repetitive flanking boundaries aligned to the reference, irrespective of intervening alignment gaps. Although separate reads of the same allelic variant might have been aligned with a gap/insertion at a different location within the repeat, the reads will all yield the same allele length call with this method. This approach effectively negates the well-known problem of large numbers of false positive SNP and indel calls resulting from inconsistent alignment of ambiguously positioned indels (Albers et al., Mills et al. 2006, Mills and Pittard et al. 2011).

Assessment of Accuracy for Genotype Calls

Two metrics, completeness and internal concordance, were employed to assess the comprehensiveness and accuracy of repeat genotype calls from whole-genome *Drosophila* data. The DGRP lines are each derived from single female founders of a natural fly population, and bred to near-isogeny by 20 generations of full-sibling matings. Therefore, although alleles may differ among lines, in the absence of mapping, alignment, or sequence errors, all reads from a single inbred line mapped to a specific microsatellite locus should possess the same repeat allele length. The assumption of homozygosity permits the use of internal concordance among the various reads within each inbred line to assess the relative accuracy of alternative approaches and tune heuristics:

$$\text{concordance} = \frac{R_{major} - 1}{R_{total} - 1},$$

where $R_{major}$=the number of reads supporting the majority allele, and $R_{total}$=the total number of scorable reads at a repeat locus.

Regions of apparent residual heterozygosity were identified in individual lines on the basis of SNP genotypes, and were excluded from concordance assessments (Mackay et al.). In conjunction with concordance, another metric, completeness, or the proportion of repeats for which valid genotypes were obtained, was employed. The combination of these two metrics enables the evaluation of the relative accuracy and the comprehensiveness of various experimental approaches and heuristics.

To assign a genotype and assess concordance for a repeat, at least two scorable reads were required. A read was determined to be "scorable" on the basis of three criteria: First, the read must span the entire microsatellite and include flanking non-repetitive sequence on both ends. Second, a minimum number (initially, one) of consecutive flanking positions adjacent to the repeat must match the reference sequence. Finally, the read must have been uniquely mapped to the reference genome, with no alternative high-scoring hits to other regions of the genome.

Most Repeats can be Genotyped Using 75 Base Paired-End Reads

The majority of the DGRP lines were sequenced using 45, 75, 95, 100, and/or 110 base reads to an average post-processed coverage of 21× (Mackay et al.). The variety of read lengths employed presented a unique opportunity to investigate how read length impacts the ability to confidently assess repeat genotypes. The concordance and completeness of microsatellite repeat genotypes as a function of the length of the repeat tract was computed, as inferred from the allele length of the reference genome (referred to henceforth as reference length). The dataset included microsatellites for which at least 80% of bases in the repeat corresponded to perfect repetitions of the repeated unit (referred to henceforth as purity).

For genomes sequenced using 45 base reads, about 50% of repeats with a reference length of 34 bases yielded genotypes and 3% of repeats with a reference length of 43 bases yielded genotypes (FIG. 3A). In comparison, for genomes that were sequenced with 75+ base reads, an average 75% of repeats with a reference length of 43 bases yielded genotypes. In the dataset, 90% of the repeats had a reference length of 22 bases or less; and 45 base reads captured 79% of genotypes for repeats with a reference length of 22. Although 45 base reads yielded high-quality genotypes for most repeats in the *Drosophila* genome, the longest repeats tend to be the most variable, and so 45 base reads are unlikely to capture the majority of repeat variation in the DGRP lines.

Read length had only a modest impact on internal concordance. For read sizes of 45, 75, and 95 bases, the concordance of repeats at all reference lengths never fell below 90% (FIG. 3B). The modest inverse correlation between read length and concordance observed for repeats shorter than ~30 bases appears to result from the higher sequence error rates in later cycles of long read sequencing (data not shown).

Figure 5:
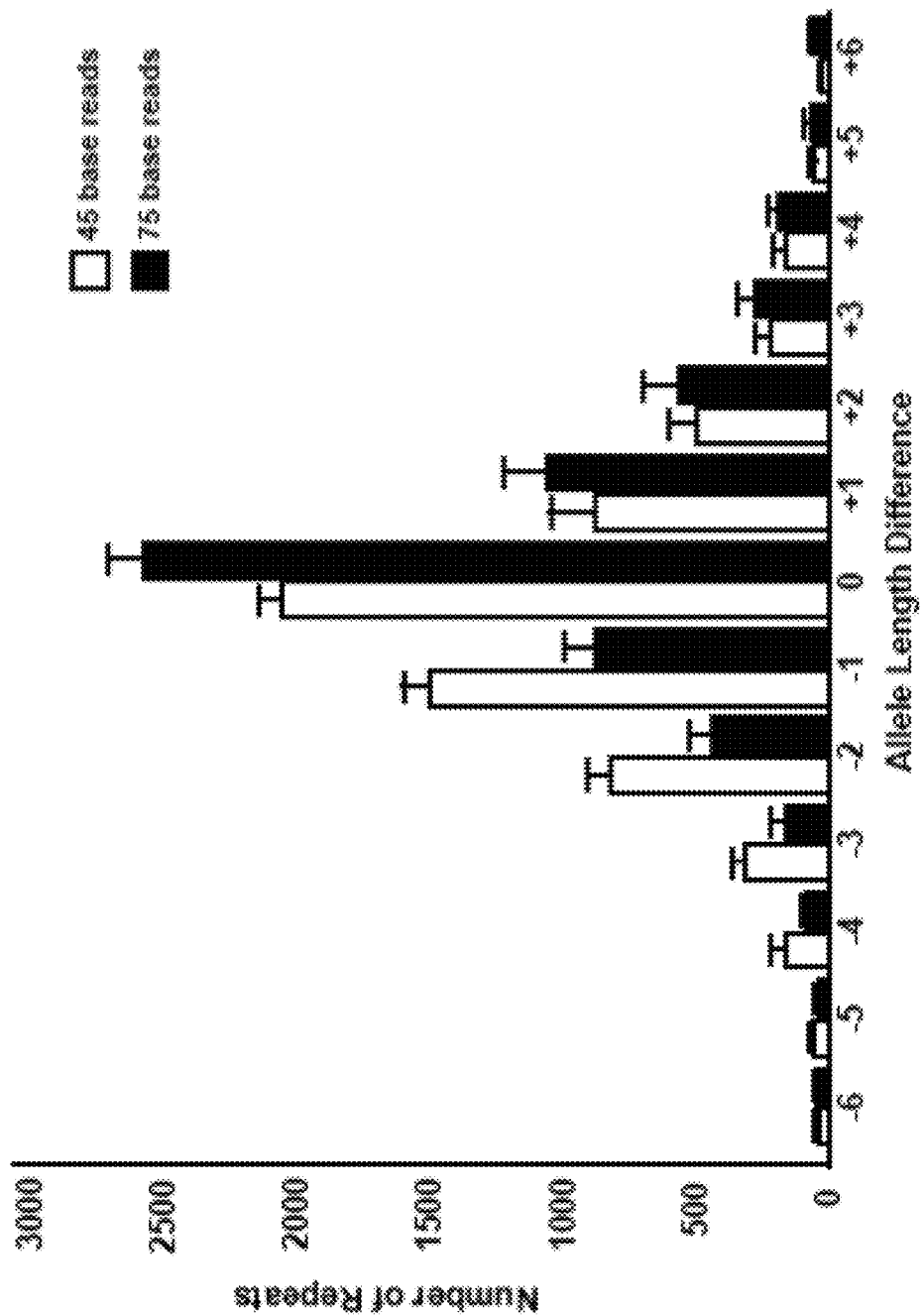
FIG. 5 depicts the number of repeats as a function of allele length difference and shows that short reads exhibit a bias towards shorter alleles. The difference between the determined genotype and the reference repeat length was tallied for 6,908 (out of 390,873) repeats for which different genotypes were obtained in the same inbred line from 45-base (open bars) versus 75-base (solid bars) reads. Permutation testing (1000 trials) indicates that the bias toward shorter alleles evident in the 45 base libraries is significant (for clarity, only the upper half of 95% confidence intervals are shown).

Some of the DGRP genomes were assembled from multiple libraries with different read lengths. In particular, there were seven genome assemblies possessing similar proportions of 45 and 75 base reads. These seven hybrid assemblies allow for direct comparisons of genotypes of the same individual derived from two read sizes. In these lines, an average of 263,994 (68%) repeats per line could be assigned genotypes using reads of both sizes. Of these, an average of 987 (0.4%) repeats per line yielded different genotypes between 45 and 75 base reads. These discordant loci exhibit a significant contraction bias in calls derived from 45 base reads, relative to the reference repeat length (FIG. 5). The contraction bias in 45 base reads is most apparent for longer repeats (data not shown), consistent with bias in ascertainment of erroneously mapped (and gapped) reads. Since 45 base reads suffer from reduced completeness for longer repeats and significant contraction bias, they were excluded from subsequent optimization and benchmarking efforts.
Genotype Accuracy is Affected by Repeat Length and Type Sequencing long microsatellite repeats is challenging and error-prone by any technology, including Sanger sequencing, with difficulties that extend beyond the known signal resolution limitations of the Roche 454 sequencing platform (Albers et al., Marguilies et al.). Homopolymeric repeats are highly prone to in vitro slippage errors during polymerase-mediated replication, and are routinely masked for next-generation sequence analyses (Hile et al.). The contribution of repeat unit size to completeness and concordance was therefore examined in order to determine unit size limitations for accurately measured changes in microsatellite repeats.

Figure 6A:
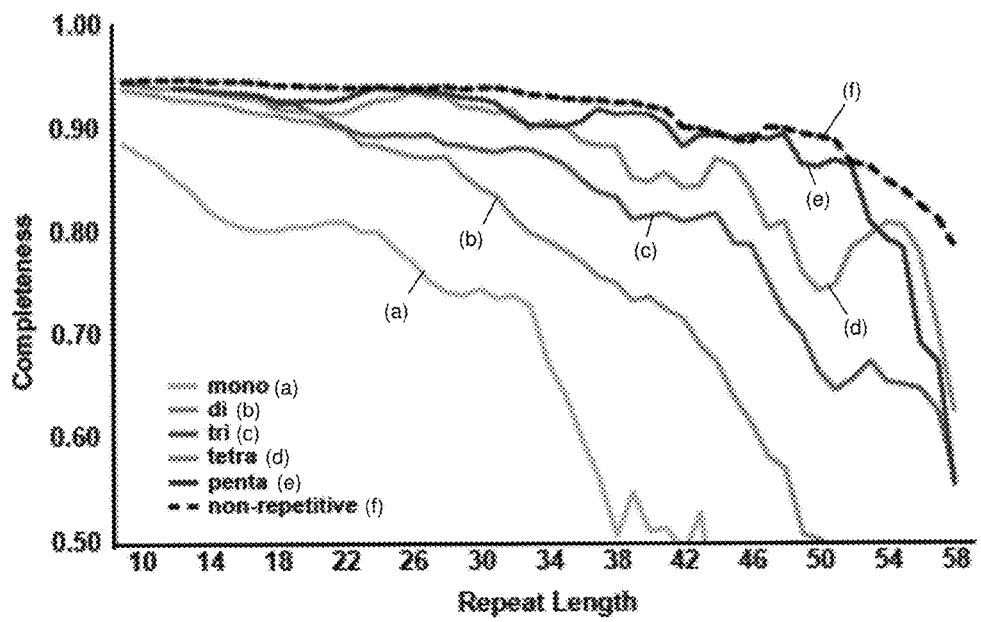
FIGS. 6A and B depict completeness (FIG. 6A) and concordance (FIG. 6B) as a function of repeat length for various repeat unit sizes, showing that shorter unit length have lower completeness (FIG. 6A) and lower concordance (FIG. 6B). The values plotted are the mean completeness or concordance values where each data point reflects an average for repeats with a reference length within 2 bases of the plotted repeat length.
Figure 6B:
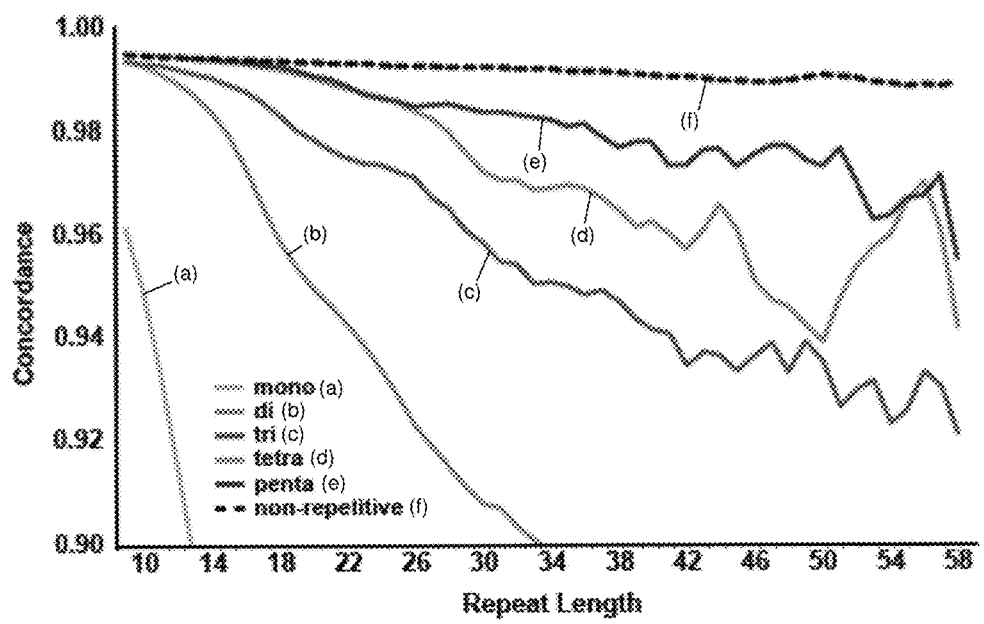

First, mononucleotide repeats were the least comprehensively genotyped repeat (FIG. 6A). In contrast, pentanucleotide repeats were genotyped with the same level of completeness as matched non-repetitive regions. Second, internal concordance for mononucleotide repeats was considerably lower than for other repeats, falling below 0.9 for homopolymers longer than 13 bases (lengths based on the reference), and to 0.8 for repeats longer than 16 bases (FIG. 6B). Completeness and concordance for longer repeat units were markedly better, with a mean concordance for dinucleotide repeats of at least 0.9 for repeats as long as 33 bases. The concordance for triplet repeats never fell below 0.92, and tetra- and pentanucleotide repeats never fell below 0.94.

Sanger sequencing was used to verify the lengths of 7 variable microsatellites, including GAGGG, ATACC, AC, A, T, and AAAT, in a total of 26 lines. These repeats were selected due to their association with startle response and starvation resistance in the DGRP lines (Mackay et al.). Sanger sequencing confirmed the genotypes of all 26 genotypes derived from the Illumina data.
Concordance is Improved by Filtering Reads with Flanking Mismatches Since regions of residual heterozygosity have been excluded, reads that span repeats in the inbred lines should all reflect the same repeat allele length. While recent de novo mutations cannot be excluded, discordant reads will predominantly be the result of errors in sequencing, mapping, or local alignment. Because microsatellites with similar or identical sequences occur at many locations in the genome, reads with repetitive sequences are more susceptible to misplacement with respect to a reference sequence. Manual inspection revealed improper mapping to be the predominant source of discordant reads. To reduce errors resulting from incorrectly mapped reads, heuristics for selectively filtering reads exhibiting characteristics indicative of mapping error were evaluated. First, the relationship between concordance and mapping quality scores obtained from the mapping software was evaluated Like most short-read mapping programs, BWA assigns a Phred-like mapping quality score to each read (MapQ) based on match uniqueness, sequence identity, end-pairing, and inferred insert size, that is intended to indicate confidence of read placement accuracy (Li and Durbin 2009, Li et al. 2008). At shorter repeat lengths (10-24 bases) the mean MapQ value for reads mapped to a locus positively correlated with concordance ($r2=0.99$, $p=0.002$). However, this correlation did not hold for repeat lengths greater than 24 bases (lengths 24-39, $r2=0.65$, $p=0.24$; lengths 40-54, $r2=0.57$, $p=0.32$). As a more sensitive test, the MapQ of discordant singleton reads for loci with at least four reads supporting the majority allele (i.e. loci with allelic representation of n:1, with n≥4) was examined. Although the MapQ scores of discordant singletons were on average 10% below the mean of the majority reads at the same locus, the score distributions were not sufficiently distinct to support effective MapQ-based filtering. Similarly, although the distribution of base sequence quality scores declined more steeply toward the end of discordant singleton reads than majority reads, the overlap in distributions limits effective read filtering on the basis of sequence quality.

Figure 7A:
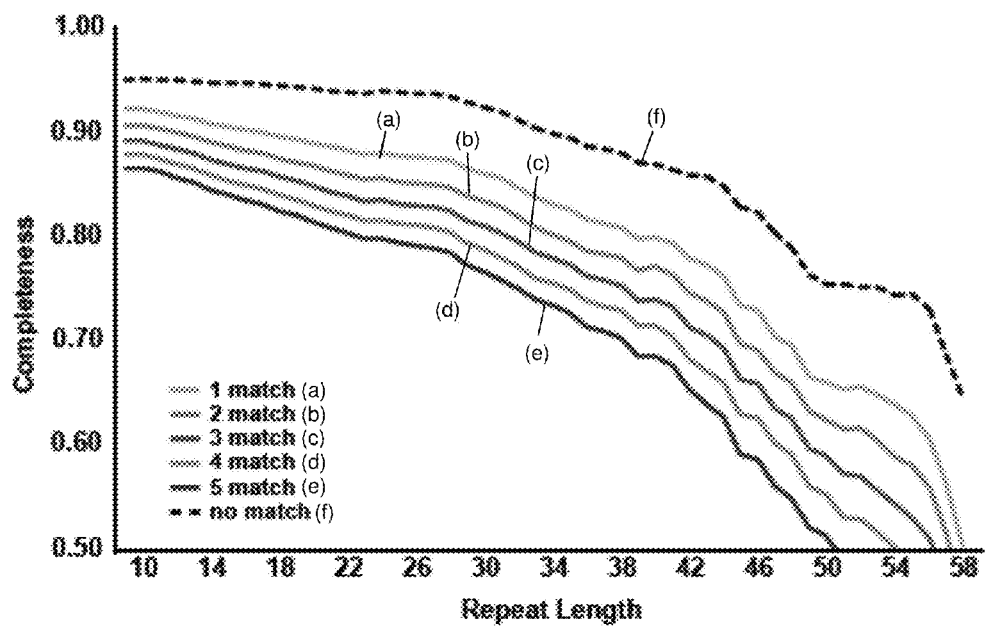
FIGS. 7A and B depict completeness (FIG. 7A) and concordance (FIG. 7B) as a function of repeat length for various numbers of required matching flank bases, showing that increasing the required number of matching flank bases between a read and the reference leads to an increase in concordance (FIG. 7A) but decrease in completeness (FIG. 7B). The minimum required number of matching flanking bases, for a read to be scored, was incremented from zero to five. Two or more scorable reads were required to determine a repeat genotype. The values plotted are the mean completeness or concordance values where each data point reflects an average for repeats with a reference length within 2 bases of the plotted repeat length.
Figure 7B:
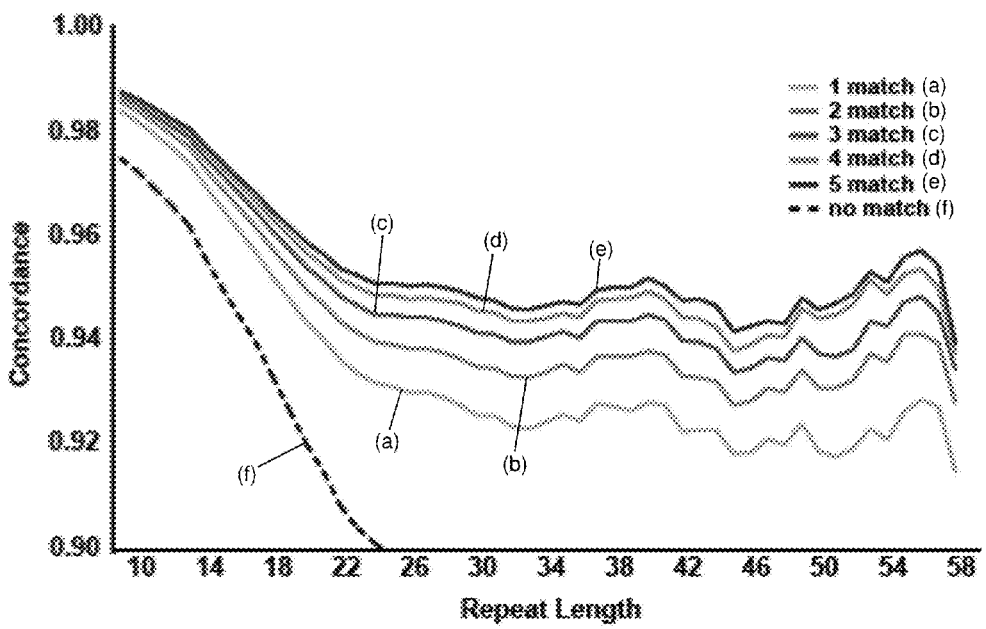
Figure 8A:
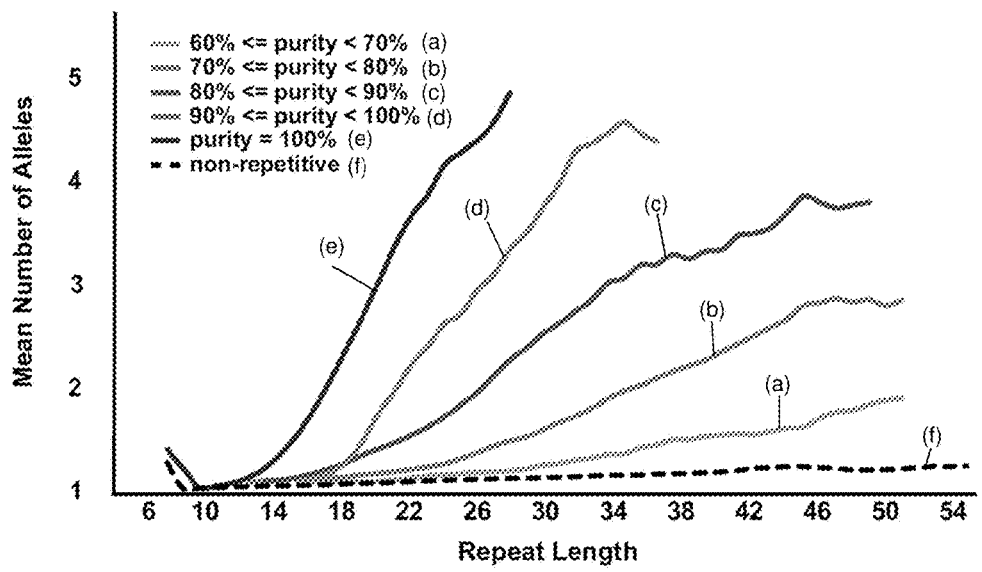
FIG. 8A depicts the mean number of alleles as a function of repeat length for various degrees of repeat purity.
Figure 8B:
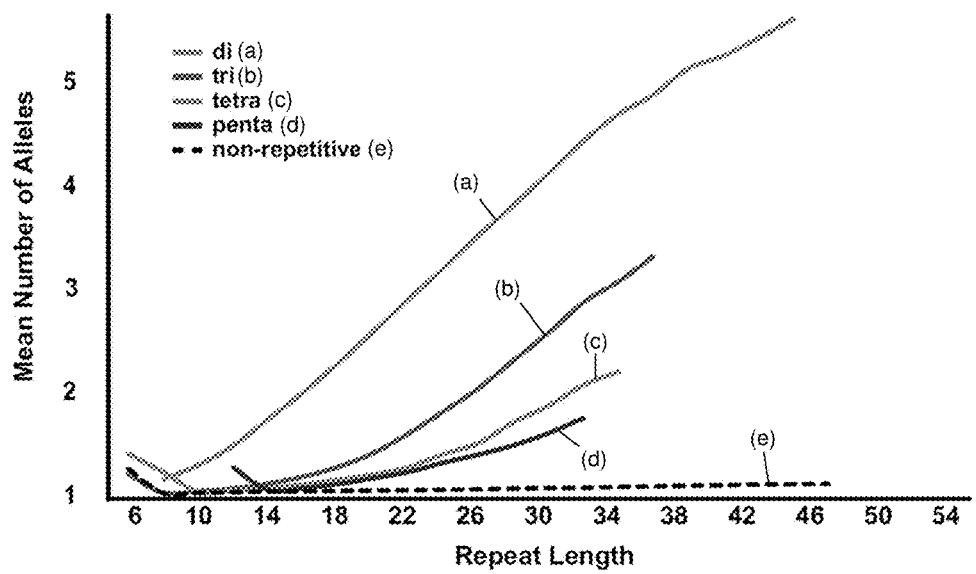
FIG. 8B depicts the mean number of alleles as a function of repeat length for various repeat unit sizes.

Manual inspection revealed that incorrectly mapped or aligned reads, and reads with poor sequence quality can often be identified by the presence of mismatches to the reference in the sequence immediately flanking the repeat. Increasing the minimum requisite number of consecutive perfectly matching flanking bases on both ends of the repeat resulted in modest drops in completeness (FIG. 7A) but substantial improvements in concordance (FIG. 7B). The improvement in concordance is exceeded by the loss in completeness when requiring more than three consecutive flanking matches.
Properties of Polymorphic Microsatellite Repeats Almost any process that exposes single strands of DNA can lead to repeat length mutations, including replication, recombination, DNA damage repair, and other aspects of DNA metabolism (Lopez et al., Wells et al.). The susceptibility of a microsatellite to length mutations is largely a function of intrinsic properties of the repeat sequence, including the repeat unit size, the number of repeated units, and the purity of the repeat tract (Legendre et al., Fondon et al. 1998). The present example shows that repeat tract length, purity, and unit size correlate with the average number of alleles for a repeat (FIG. 8). The relationship between purity and length reveals that repeats possessing only one or two interruptions (FIG. 8A, line (d)) evolve similarly to perfect repeats ~6-8 nucleotides shorter (FIG. 8A, line (e)), corresponding closely to the expected longest uninterrupted stretch of the imperfect repeats. However, a different dynamic emerges for more degenerate repeats, which exhibit step-wise decreases in slope with purity, yet all with similar intercepts. This pattern is not explained by uninterrupted segments of imperfect repeats, potentially suggestive of alternate mechanisms. In addition, dinucleotide repeats segregate from other repeats as the most variable (FIG. 8B).

Since microsatellite length mutations almost always give rise to insertions or deletions of one or more whole repeat units, the minimum lengths at which short tandem repeats begin to exhibit this form of mutation can be determined by the emergence of excess unit-length variants over background mutation rates for nearby non-repetitive sequences. Makova and colleagues (Kelkar et al.) recently used a related approach to delimit length thresholds for microsatellites within several regions Sanger sequenced in humans as part of the ENCODE project. In that study, the authors determined that human mononucleotide and dinucleotide repeats mutate above background slippage rates when the repeat tract is at least 10 bases (Kelkar et al.).

Figure 9:
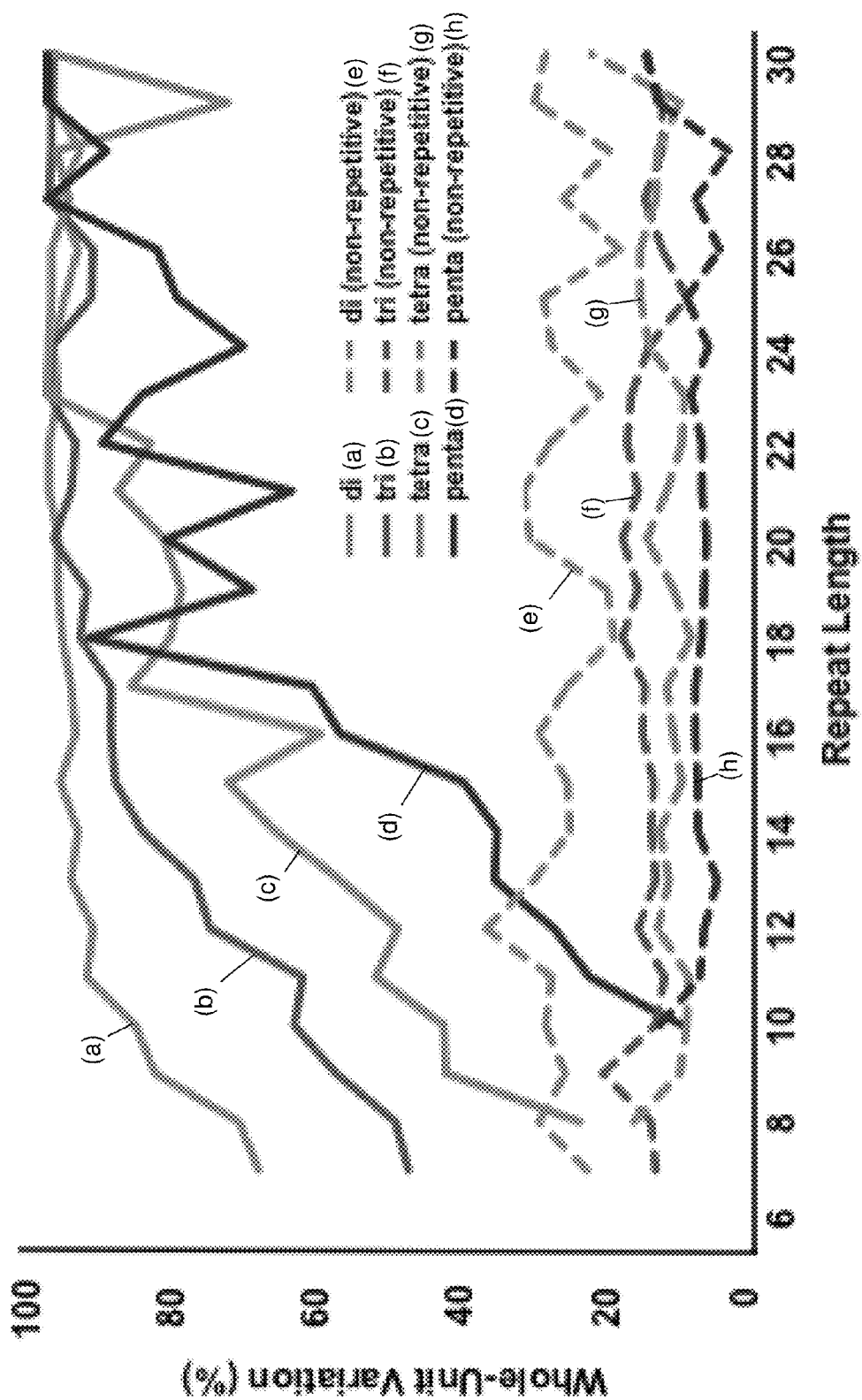
FIG. 9 depicts whole-unit variation versus repeat length for various repeat unit sizes. The tendency for changes in repeat length to occur in the form of insertions and deletions of whole repeated units increases with tract length. The percent in-phase values of uninterrupted 2mer, 3mer, 4mer, and 5mer repeats approached a plateau at repeat lengths of 13, 20, 23, and 27 bases respectively, where length-changes are close to 100% in-phase. Genotypes for pure repeats were determined in all the DGRP lines if there were at least two scorable reads and a read was scored if it spanned the repeat region with 3 or more matching flank bases on either side of the repeat.

The lengths at which various repetitive sequences begin mutating as microsatellites was determined by examining how the proportion of whole-unit variation to non-whole-unit variation changes as a function repeat length. Repeat variation from the DGRP lines was classified in the form of the proportion of alleles that differ in whole-unit lengths from the most common allele relative to fractional unit length differences. As shown in FIG. 9, the tendency for repetitive sequences to mutate in whole unit increments is clearly evident for even very short repeats. This tendency increases rapidly with tract length and eventually begins to plateau at approximately 13, 20, 23, and 27 bases for di-, tri-, tetra-, and pentanucleotide repeats, respectively. Most of the variation (97%, 96%, 82%, and 86%, for di-, tri-, tetra-, and pentanucleotides), in repeats at least as long as these plateau lengths, conforms to the classic step-wise model of microsatellite evolution (FIGS. 10A-D). The majority of repeat lengths that were not whole-unit likely reflect errors in sequencing, mapping, or alignment. However, it is possible that some of this non-unit variation might also be indicative of other classes of indel mutations; or they might reflect instances of complex or imperfect repeats exhibiting mutational properties of multiple different units. Examples of the former possibility are most evident among tetranucleotide repeats, for which a large proportion of non-whole-unit variation is in multiples of two bases (FIG. 10C). This half-unit excess is predominantly produced by imperfect repeats, but is also apparent in many perfect tetranucleotide repeats, suggestive of an alternative mutational process. Finally, although strand-slippage is expected to induce whole-unit mutations in uninterrupted repeats, repeats are also prone to double-strand breaks and if these breaks are not repaired by recombination-mediated processes, non-whole-unit changes to repeats can result (Mittelman et al., Axford et al.).

Discussion

Nucleotide repeats are ubiquitous and polymorphic across all species. An often-cited example of physiologically and evolutionarily important microsatellite variation in *Drosophila* is a polymorphic threonine-glycine dipeptide repeat within the period gene. Naturally occurring length variation of the period coding repeat gene produces altered temperature-dependent circadian rhythm behavior in related populations of flies (Sawyer et al.). Natural selection has been demonstrated to act upon this locally adaptive variation, and it has been proposed that variation in such rhythm behavior underlies sympatric speciation events (Karol et al.). Furthermore, microsatellite repeats likely underlie the evolution of quantitative traits in many other species including mammals (Gemayel et al.).

Figure 11A:
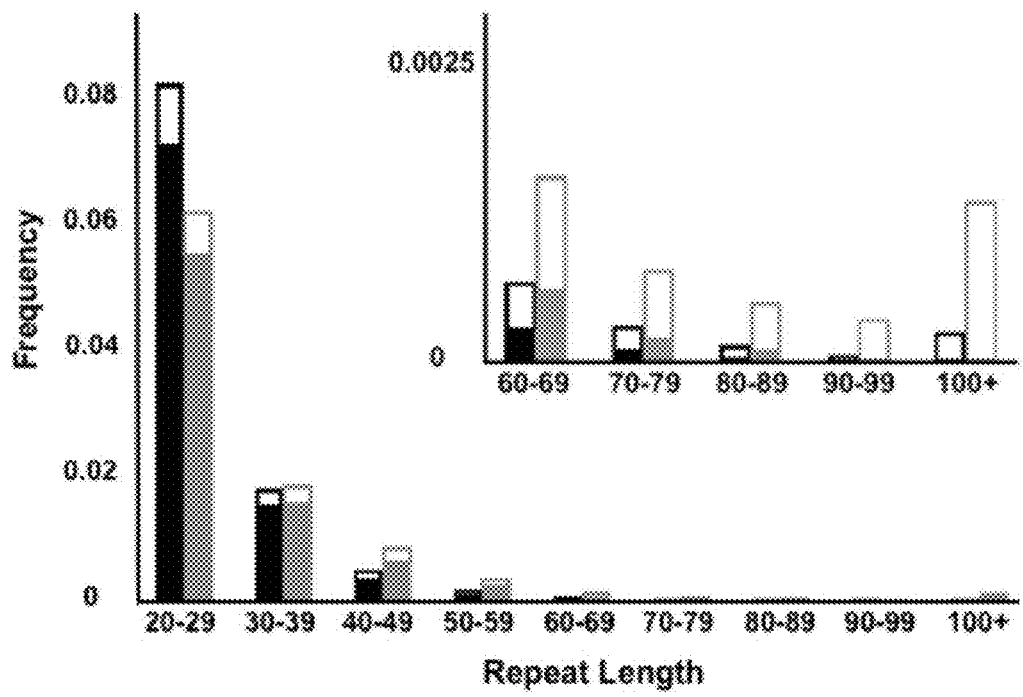
FIGS. 11A and B depict the distributions of repeat lengths in *Drosophila* and human genomes. The heights of the bars indicate the frequency of repeats at various lengths.
Figure 11B:
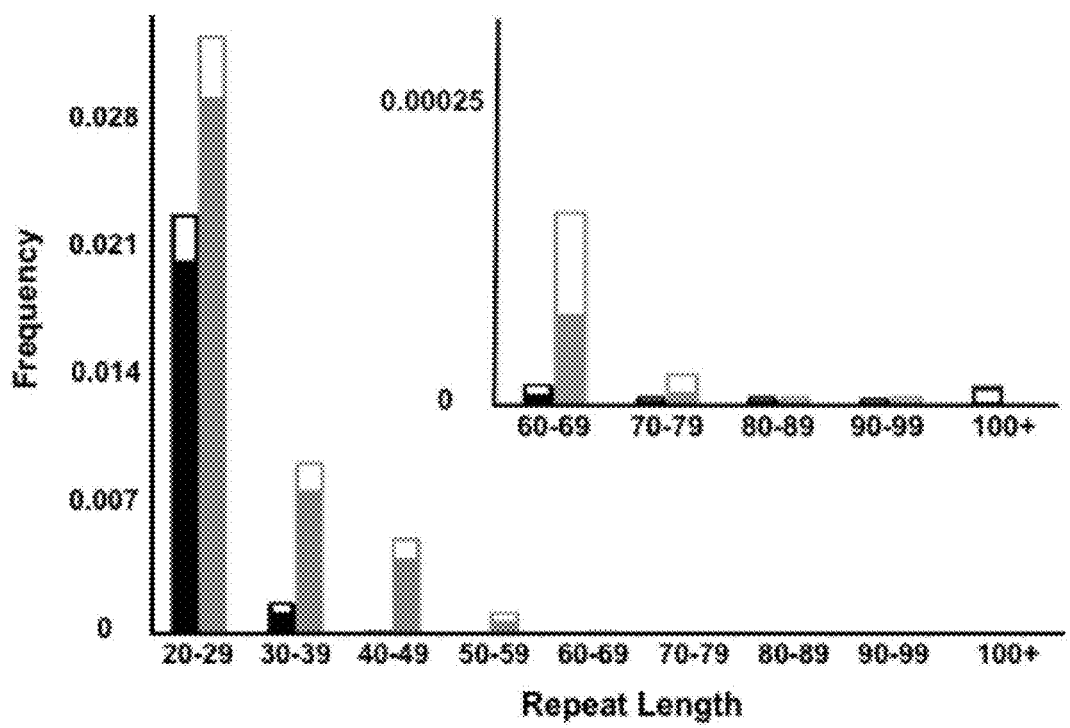
FIG. 11B shows the frequency of pure repeats. The solid portions indicate the fraction repeats that can be genotyped based on measurement of completeness described herein using reads that are at least 100 bases. *Drosophila* data is plotted with black bars and human data is plotted with gray bars. The insets depict the frequency values of repeat lengths of 60-69 through 100+ at greater resolution.

The present example shows an approach to derive microsatellite repeat allele lengths from Illumina whole-genome data to gain insight into the mutational processes that modulate microsatellite variation and to enable the discovery of functional microsatellites. The example shows that read sizes of at least 75 bases are sufficient to enable the accurate genotyping of most repeats in the *Drosophila melanogaster* genome and that mononucleotide repeats are the most challenging repeats to measure. The approach shown in the present example will gain even more utility for the ongoing data deluge as the read lengths for Illumina data now approach 150 bases. The approach can also be generalized to other genomes, including human genomes. Although the length distribution of microsatellites is longer in mammals than in *Drosophila* (Schug et al.), repeats in normal human genomes, for example, almost never exceed 75 bases for pure repeats (FIG. 11B) or even imperfect repeats (FIG. 11A).

In the population of 158 inbred isolates from the *Drosophila* Genetics Reference Panel, the example shows that a third of the identified repeats vary in the population. Some of these repeats have already been related by GWAS to traits such as startle response and starvation resistance in the DGRP lines (Mackay et al.). Undoubtedly, future studies with the DGRP population will reveal other associations between repeat length changes and trait variation. Next, the example shows that these polymorphic repeats follow accepted models for repeat instability—repeat mutation predominantly manifests itself in the form of insertions or deletions of whole repeat units and polymorphism correlates with increasing length and sequence purity. Finally, the example used the DGRP dataset to ascertain the minimum lengths for a repetitive sequence to mutate as a microsatellite and found these values to be 13, 20, 23, and 27 bases for di-, tri-, tetra-, and penta-nucleotide repeats respectively.

While the above results establish a proof of principle that microsatellite repeats can be genotyped from short read next-generation sequencing data, another goal of the example is to show how microsatellite variation in the DGRP lines or other organisms, such as humans, can be cataloged to enable future studies of their contributions to variation in morphological, behavioral, and life-history traits.

Example 2—Accurate Human Microsatellite Genotypes from High-Throughput Resequencing Data Using Informed Error Profiles Summary Repetitive sequences are biologically and clinically important because they can influence traits and disease, but repeats are challenging to analyze using short-read sequencing technology. The present example presents a system for genotyping microsatellite repeats, which uses Bayesian model selection guided by an empirically derived error model that incorporates sequence and read properties. Next, the present example applies the system to high-coverage genomes from the 1000 Genomes Project (1000 Genomes Project Consortium, *Nature* 2010) to evaluate performance and accuracy. The system assigned genotypes to ~90% of the repeat loci, including homopolymers. In addition, comparing the system to lobSTR revealed that ~90% of repeats genotyped by both methods were assigned the same call. The system in the present example is implemented as software. The software inputs high-throughput resequencing data in BAM format (Li and Handsacker et al. 2009) and outputs genotypes in multiple formats, including VCF format (Danecek et al.), for compatibility and easy integration with existing genotyping pipelines. Exemplary source code and binaries for the software are available at github.com at the /adaptivegenome/repeatseq subdomain.

Methods

Outline of the System

Figures 12A, 12B:
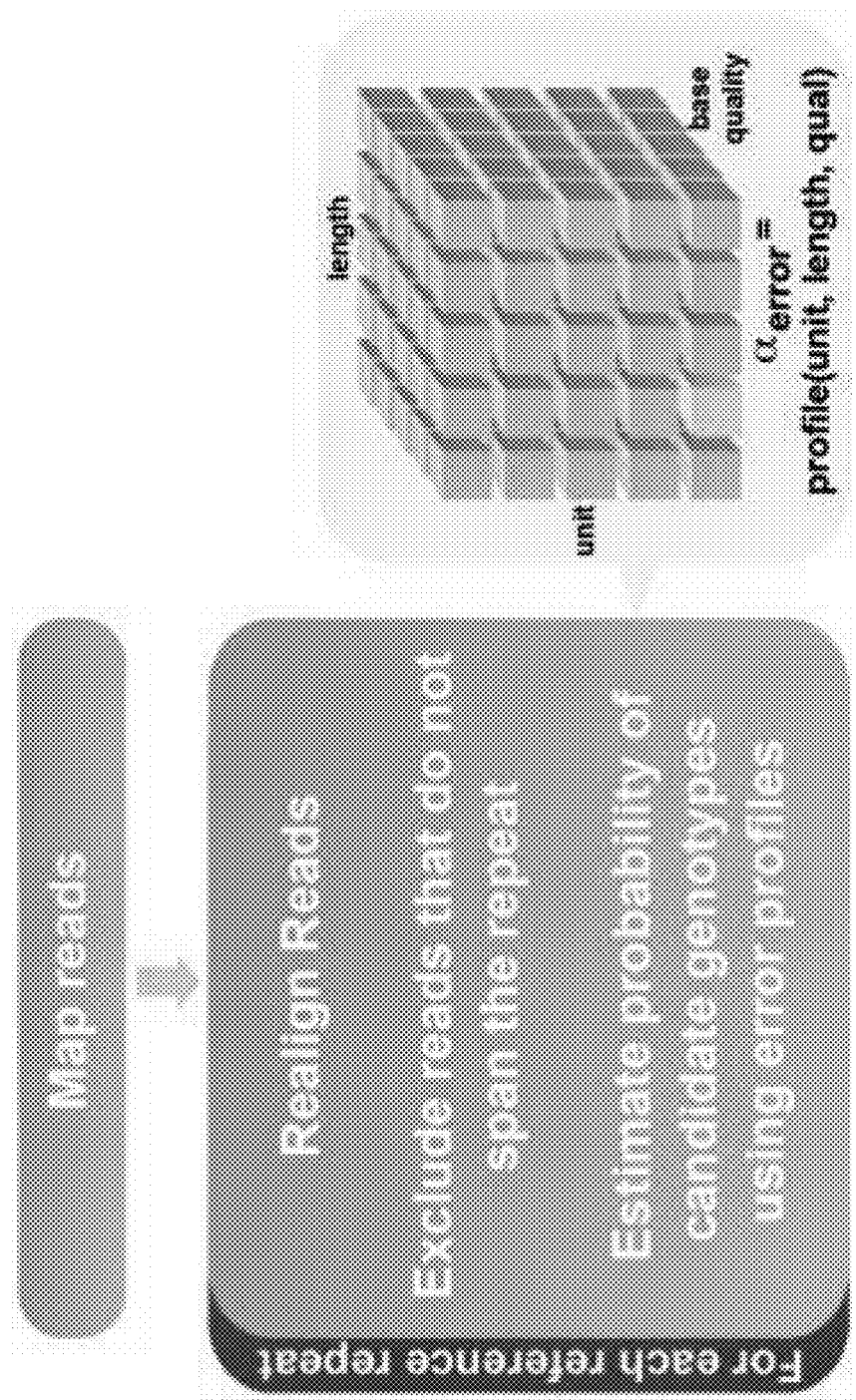
FIG. 12A depicts an outline of an exemplary method of the present invention. Reads are mapped and realigned, and a set of reads spanning reference repeats are retained. Genotypes are assigned with consideration of the a priori error rate $\alpha_{error}$, which comes from the appropriate error profile and is used in the prior distribution of allele and error probabilities $\pi(\vec{\theta} \mid \vec{\alpha}, g_i)$. The probability of each genotype suggested by the data is estimated in a Bayesian fashion, and the most probable genotype among these is called.
FIG. 12B shows a schematic of exemplary array of bins of various repeat lengths, repeat unit sizes, and average base qualities and associated discordant and concordant read frequencies associated therewith.

The genotyping process is summarized in FIG. 12A. Reads are first mapped to a reference sequence and then sorted, with duplicate reads marked. Next, reads mapping to reference repeat regions are locally realigned using the GATK IndelRealigner tool. Then, for each repeat, the system module discards reads that do not completely span the repeat, as these reads cannot unambiguously support a repeat allele length. The extent to which a read must overlap a repeat (and match the reference) is an adjustable parameter, although this value has been optimized to maximize the number of repeat regions that could be genotyped while minimizing the inclusion of improperly mapped reads (see Example 1). Finally, the system assigns the most probable genotype using a fully Bayesian approach and considers the reference length of the repeat, the repeat unit size and the average base quality of the mapped reads, as previous information. The system implements a diploid genotyping model by default, but it can be set at runtime to implement a haploid model.

Several other read filters can be adjusted. For example, reads can be excluded from consideration on the basis of their length, mapping quality and on whether they are properly paired. By default, the system returns microsatellite calls in VCF format for compatibility and interoperability with other indel callers. However, the system can also output a detailed report that returns annotated alignments of reads in addition to just the assigned genotypes.

Probabilistic Determination of Repeat Genotypes

The probability that a read is representative of a true allele can be inferred by the properties of the read and the reference repeat sequence that it maps to (see Example 1). The DGRP is composed of >100 fly genomes; each derived from single female founders of a natural fly population and bred to near-isogeny by 20 generations of full-sibling matings. Therefore, in the absence of mapping, alignment or sequence errors, all reads from a single inbred line mapped to a specific microsatellite locus should possess the same repeat allele length, and this homozygosity permits the assumption that deviant reads represent error. To strengthen the validity of this assumption, the effects of any residual heterozygosity was minimized by excluding genomic regions with >5% heterozygosity (based on the SNP calls). For loci to which at least 10 reads had been mapped, reads that supported the majority allele were assumed to support the true allele at the locus, whereas reads that supported a non-majority allele were assumed to be errors. The proportions of reads supporting majority alleles were computed within five bins of equal size for the following properties: reference repeat length, repeat unit size, and average base quality for the read. The resulting 5×5×5 array reflects the frequency of discordant and concordant reads and is the source of error profiles for the system (FIG. 12B).

Once reads are mapped, realigned and then pruned of those that do not span the repeat, the system calls the most probable genotype using Bayesian model selection. The error rate ($\alpha_{error}$) is populated with prior information by associating the reference repeat length, unit size, and average base quality of the read data with the appropriate bin of the error profiles. The reads at a given locus support k length variants $v_1, v_2, \ldots, v_k$ where $k \geq 1$. The system considers each homozygous and heterozygous genotype suggested by the read data, of which, there are $c = k(k+1)/2$. For example, if two length alleles are present then the heterozygous genotype of the two variants and each homozygous genotype are considered. If three variants are present, then the possible three homozygous and three heterozygous genotypes are considered.

Let x denote the reads at a given locus. Denote the c possible genotypes $g_1, g_2, \ldots, g_c$. For heterozygous and homozygous genotypes, the likelihood $L(\vec{x}|g_i)$ is assumed as multinomial (n, $\vec{\theta}$), and $\pi(\vec{\theta})$ is Dirichlet ($\vec{\alpha}$), where the elements of $\vec{\theta}$ sum to unity. For the purpose of elucidating the statistical model, let $g_A$ generically denote a homozygous genotype and let $g_{AB}$ denote a heterozygous genotype, where A and B each represent one of the length variants present in the data. In the heterozygous case, the values $\vec{x}$, $\vec{\theta}$ and $\vec{\alpha}$ are 3D vectors. The values $x_{(1)}$ and $x_{(2)}$ represent the number of reads of variants A and B, respectively, and $x_{(3)}$ is the number of reads of any other variant. Values $\theta_{(1)}$ and $\theta_{(2)}$ represent the probability that a read at this locus is of variant A and B, respectively, and $\theta_{(3)}$ represents the probability that a read does not represent a true variant (e.g. a sequencing or mapping artifact relative to the genotype $g_i$ under consideration). The homozygous genotypes are modeled similarly with 2D vectors: position one refers to the variant supported by the genotype and the second position refers to all other alleles.

The vector $\vec{\alpha}$ characterizes prior information about the probability vector $\vec{\theta}$, and $\vec{\alpha}$ is formed based on derived error profiles. In the heterozygous case, let $y_A$ represent the number of majority allele supporting reads of variant A from the error profiles, and let $w_a$ represent the number of non-majority allele supporting reads from the error profiles. Let $y_B$ and $w_B$ be similarly defined for variant B. Hyperparameters $\alpha_{(1)} + \alpha_{(2)} = 1 + (y_A + y_B)/2$ and $\alpha_{(3)} = \alpha_{error} + 1 + w_A + w_B$. In the homozygous case, hyperparameters $\alpha_{(1)} = 1 + y_A$ and $\alpha_{(2)} = \alpha_{error} + 1 + w_A$, where $y_A$ and $w_A$ are as defined previously. The Bayesian model describing the probability of read error given genotype g, is as follows:

Prior: $\pi(\vec{\theta} | \vec{\alpha}, g_i)$ is Dirichlet($\vec{\alpha} + 1$)

Likelihood: $L(\vec{x} | \vec{\theta}, g_i)$ is multinomial(m, $\vec{\theta}$), hence Posterior: $\pi(\vec{\theta} | \vec{x}, \vec{\alpha}, g_i)$ is Dirichlet($\vec{\alpha} + \vec{x} + 1$)

This model specification ensures that the posterior distribution $\pi(\vec{x} \vec{\theta}, \vec{\alpha}, g_i)$ weighs the error profile reads equally to reads from the data. The aforementioned model specification for all genotypes $g_i = 1, \ldots, c$ is considered. The marginal distribution of the data given each genotype is estimated, and Bayes' rule is used to compute the probability of each genotype given the data. This strategy is a fully Bayesian model selection algorithm, for which each model under consideration corresponds to one of the genotypes suggested by the data. The marginal distribution of the data for a given genotype is $$\pi(\vec{x} | g_i) = \frac{B(\vec{\alpha} + \vec{x} + \vec{1})}{B(\vec{\alpha} + \vec{1})} * \frac{n!}{\prod_{j=1}^{k} x_j!}$$

where B(•) represents the multinomial beta function. This analytical solution is based on conjugacy results. Bayes' rule is then implemented to invert the above probabilities.

$$\pi(g_i | \vec{x}) = \frac{\pi(\vec{x} | g_i)\pi(g_i)}{\sum_{j=1}^{k} \pi(\vec{x} | g_j)\pi(g_j)}$$

where $\pi(g_i) = 1/k$ for all $i = 1, \ldots, k$. The most probable genotype is then selected, provided that the probability of the genotype is >50%.

Results

Optimization of Read Mapping for Microsatellite Repeat Genotyping

The accuracy of repeat genotypes is contingent on the proper mapping of reads to repeat loci. There are many short-read mapping algorithms, and their performance has been widely evaluated (Li and Homer 2010). However, mapping algorithms have not yet been evaluated on their ability to accurately map reads composed of low-complexity sequence. The accuracy of several popular tools, including Bowtie2 (Langmead et al.), BWA (Li and Durbin 2010), Novoalign (Novocraft Technologies), Stampy (Lunter et al.) and SMALT (Wellcome Trust Sanger Institute) were compared. First, reference repeats were identified from the hg19 reference sequence using the approach outlined in Example 1. Next, DWGSIM (github.com at the /nh13/DWGSIM subdomain) was used to simulate 100 bp single-end Illumina reads from reference repeats from chromosomes 1 through 7 in human reference sequence, with a simulated coverage of 15×. A 2% uniform sequencing error rate and a 0.1% mutation rate were specified, of which 10% of the mutations were small indels (1-10 bp long) and the remainder were point mutations.

Figure 13:
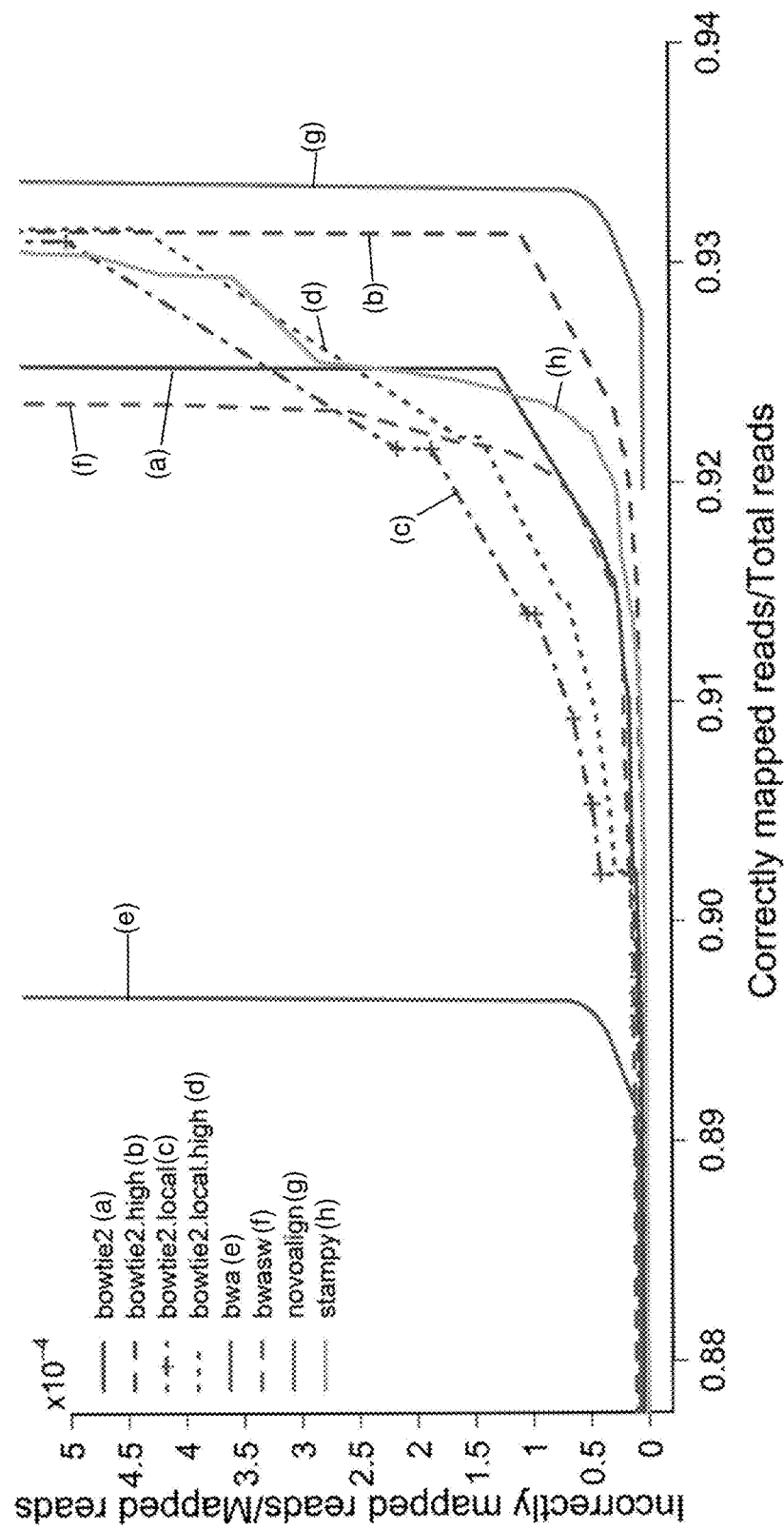
FIG. 13 shows the performance of various methods for mapping reads to reference repeats. Mapping accuracy is determined using simulated 100 bp Illumina reads (with a coverage of 15×) and is assessed by measuring the proportion of incorrectly mapped reads as a function of the proportion of correctly mapped reads under different mapping quality thresholds. Variations of Bowtie2 are fully described as follows: bowtie2 (Bowtie2 with default settings), bowtie2-high (Bowtie2 using the highest sensitivity setting), bowtie2-local (Bowtie2 with default sensitivity and soft-clipping) and bowtie2-local-high (Bowtie2 using the highest sensitivity and soft-clipping).

Simulated reads were then mapped to the entire human reference sequence. The proportion of incorrectly mapped reads is plotted as a function of the proportion of correctly mapped reads in FIG. 13 under different mapping quality thresholds. For each mapping quality threshold, the accuracy rate is the number of correctly mapped reads divided by the total amount of reads simulated. Likewise, the inaccuracy rate is the number of incorrectly mapped reads divided by the total number of mapped reads. Assessment of read alignment is based on the leftmost coordinate of the read. Novoalign maps repeat-containing reads with the lowest ratio of inaccurate calls to accurate calls. Among the open source tools, Bowtie2-high (Bowtie2 using the highest sensitivity option) is the best mapping method by this metric. Other settings of Bowtie2, along with Stampy and BWA-SW, performed fairly similarly among each other, but not as well as Novoalign or Bowtie2-high.

Table 2 summarizes the performance of the mapping programs and includes a comparison with the lobSTR method, which eschews conventional short-read mappers in favor of its own method for directly assigning reads to a proper location on the human reference sequence. The table indicates performance cumulatively for all mapping qualities, to enable fair comparison with lobSTR, which does not report mapping quality. Novoalign mapped the greatest number of correctly mapped reads (40,547,527; 93.9%), although SMALT mapped the greatest number of reads overall (41,180,368; 95.4%). LobSTR mapped the fewest number of correctly mapped reads (1,117,142; 2.59%) but also the fewest reads overall (1,118,902; 2.59%). Maximizing read mapping might result in increased numbers of improperly mapped reads; therefore, mapping methods were also compared on the basis of their inaccuracy rate. It was found that lobSTR features the lowest inaccuracy rate of 0.16%, followed by Novoalign with an inaccuracy rate of 1.14%. The open-source Bowtie2-high method also performs nearly as well with an inaccuracy rate of 1.18%.

Comparing performance cumulatively for all mapping qualities likely underestimates the accuracy of conventional mappers because even minimal filtering by mapping quality can exclude inaccurately mapped reads. For example, filtering reads based on a minimum mapping quality of 4 lowers the Novoalign inaccuracy rate to 0.007%, at the cost of reducing the number of correctly mapped reads to 40,297, 714 (93.3%). At a minimum mapping quality of 3, Novoalign features an inaccuracy rate of 0.33% with 40,436, 553 (93.6%) correctly mapped reads. Bowtie2-high performs similarly with an inaccuracy rate of 0.03% (40,213, 461 or 93.1% correctly mapped reads) with a minimum mapping quality of 2. Filtering reads by mapping quality allows for optimizing the trade-off of maximizing correctly mapped reads while minimizing the incorrectly mapped reads.

Application of the Present System to Whole Genomes from a Parent-Offspring Trio

A subset of genotyping error can be inferred by evaluating whether called genotypes from a parent-offspring dataset are consistent with Mendelian inheritance (Douglas et al.). The present system was applied to whole genome data generated using the Illumina HiSeq and 100 bp reads, from the CEU trio, a family from Utah with European ancestry (CEU genomes: NA12878, NA12891, NA12892). The average coverage of the mapped and post-processed genomes was 42.7× and this coverage dropped to 33.3× at repeat regions. In testing for consistency with Mendelian inheritance, repeats for which calls were made from all genomes in the trio and for which there was at least a single mapped discordant read at the locus in each genome were considered. The system required at least two reads to make a call and for this threshold, 92.1% of evaluated repeat calls are consistent with Mendelian inheritance. At a minimum coverage of 9×, the percentage of consistent calls increases to 95.3%, and at 17×, the percentage increase to 98.0%.

This consistency test also enables the assessment of the impact of choosing a less informative prior for the genotyping model. The error profile of the present system was replaced with a constant rate prior in which a single observed concordant read and no discordant reads were defined for every element of the error profile. This strategy eschews the experimentally derived error profile and instead incorporates weak prior information into the genotyping algorithm. Not surprisingly, the percentage of consistent calls drops substantially. At a minimum of 2, 9 and 17×

TABLE 2

Performance of mappers for microsatellite repeat regions[a]

| Method | Total mapped n (%) | Correctly mapped n (%) | Incorrectly mapped n (%) |
|---|---|---|---|
| lobSTR | 1,118,902 (2.59) | 1,117,142 (2.59) | 1,760 (0.16) |
| Novoalign | 41,014,531 (95.0) | 40,547,527 (93.9) | 467,004 (1.14) |
| Bowtie2 | 40,678,703 (94.2) | 40,196,603 (93.0) | 482,100 (1.19) |
| Bowtie2-high | 40,946,152 (94.8) | 40,464,488 (93.7) | 481,664 (1.18) |
| Bowtie2-local | 40,961,622 (94.9) | 40,448,448 (93.6) | 513,174 (1.25) |
| Bowtie2-local-high | 40,975,438 (94.9) | 40,472,990 (93.7) | 502,421 (1.23) |
| BWA | 39,390,695 (91.2) | 38,941,969 (90.2) | 448,726 (1.14) |
| BWASW | 40,611,633 (94.1) | 40,120,872 (92.9) | 490,761 (1.21) |
| SMALT | 41,180,368 (95.4) | 40,491,179 (93.7) | 689,189 (1.67) |
| Stampy | 41,004,163 (95.0) | 40,478,030 (93.8) | 526,133 (1.28) |

[a]Number (%) of total, correctly and incorrectly mapped reads by each mapping method from 43,176,537 simulated 100 bp single-end reads that overlap a repetitive region in the hg19 reference sequence. Percentages for incorrectly mapped reads are from total mapped reads and not the total simulated reads.

coverage, the constant rate prior produces calls that are consistent 72.9, 73.7 and 74.5% of the time, respectively.
Application of the Present System to the HG01140 Whole Genome The performance of the present genotyper was compared with lobSTR, a recently reported tool that is also the only other genotyper tuned for microsatellite repeats. To perform the comparison, a 16× sequenced human genome (HG01140) from the 1000 Genomes Project was mapped against the hg19 reference sequencing using Novoalign, post-processed and passed to both genotyping methods. The FASTQ files for this genome were mapped using Novoalign and realigned using the GATK IndelRealigner. The present system was then executed using default parameters to generate a list of repeat genotypes. To genotype repeats with lobSTR, the available binaries (lobSTR version 1.0.6) and usage guidelines were used. First, lobSTR built an index for the hg19 reference genome. The same list of repeat regions used by the present system was indexed for use by lobSTR. Next, lobSTR constructed a new BAM file (based on the same BAM file used by the present system) containing its alignments for genotype calling. Default parameters were used except that genotyping repeats with a unit length of 1-5 was specified. The lobSTR-generated BAM file was then passed to the lobSTR allelotyper tool to produce a list of repeat genotypes.

Table 3 summarizes the comparison of the present system and lobSTR genotypes. The percentages indicate the fraction of genotypes made from a list of 4,030,980 reference repeat regions. Unlike the earlier comparison using simulated data from chromosomes 1 through 7, this comparison includes all identified hg19 reference repeat regions. The present system assigned genotypes to 3,604,790 (89.4%) repeats, whereas lobSTR assigned genotypes 106,043 (2.63%) repeats. When the comparison is made by repeat unit size, the presented system assigns genotypes to a similar proportion of repeats for all unit sizes, whereas lobSTR assigned the most genotypes to dinucleotide repeats (64,670; 10.3%). For repeat regions that were genotyped by the present system and lobSTR, the concordance of the methods or cases in which both methods assigned the same genotype was measured. Genotypes were assigned by both methods for 96,950 repeats. Of these, 85,569 (88.3%) repeat genotypes were the same. The concordance between the methods is lowest for 2mers (83.4%) and increases with unit size, which is expected given that the variability of microsatellite repeats is dependent on the size of the repeated unit sequence. From the 11,381 (11.7%) discordant genotypes, repeat regions were randomly selected and Sanger sequencing was used to confirm which method assigned the correct genotype. After sequencing 40 regions, it was found that 25 (62.5%) regions were correctly genotyped by the present system, 4 (10.0%) regions were correctly genotyped by lobSTR and 11 (27.5%) regions were incorrectly genotyped by both methods.

TABLE 3

Comparison of the present system and lobSTR microsatellite calls[a]

| Comparison | 1 n (%) | 2 n (%) | 3 n (%) | 4 n (%) | 5 n (%) | Total n (%) |
|---|---|---|---|---|---|---|
| Present System calls | 1 014 806 (88.0) | 556 727 (89.0) | 680 939 (89.7) | 766 010 (90.6) | 586 308 (90.7) | 3 604 790 (89.4) |
| lobSTR calls | N | 64 670 (10.3) | 15 722 (2.07) | 17 336 (2.05) | 8315 (1.29) | 106 043 (2.63) |
| Concordant call | N | 47 987 (7.67) | 14 482 (1.91) | 15 430 (1.82) | 7670 (1.19) | 85 569 (2.12) |
| Discordant call | N | 9538 (1.52) | 624 (0.08) | 946 (0.11) | 273 (0.04) | 11 381 (0.28) |
| Present system call, lobSTR N | 1 014 806 (88.0) | 499 202 (79.8) | 665 833 (87.7) | 749 634 (88.6) | 578 365 (89.5) | 3 507 840 (87.0) |
| lobSTR call, present system N | N | 67145 (1.14) | 616 (0.08) | 960 (0.11) | 372 (0.06) | 9093 (0.23) |
| Present system N, lobSTR N | 138 769 (12.0) | 61 800 (9.88) | 77 758 (10.2) | 78 922 (9.33) | 59 848 (9.26) | 417 097 (10.3) |

[a]Number (%) of total, concordant and discordant microsatellite calls are provided by repeat unit size, indicated by column values 1-5. Comparisons are made for microsatellites in which both, one or neither method makes a call.
N indicates no call.

From the 3,604,790 repeat genotypes assigned by the present system, lobSTR failed to genotype 3,507,840 (97.3%) regions. This is consistent with lobSTRs greatly reduced number of total and correctly mapped reads for the simulated data (Table 2). However, from the 106,043 repeat genotypes assigned by lobSTR, 9093 repeat genotypes (8.57%) were missed by the present system. In 5,090 (56.0%) of the repeats, lobSTR was able to map more reads to the locus than the present system had access to, and this likely enabled the assignment of a genotype by lobSTR. In nearly half of these cases (2436 repeats), lobSTR added more than one mapped read to the locus. It was also found that lobSTR assigns genotypes if at least a single read is mapped to the locus. The present system, however, requires at least two mapped reads, as a single read is not sufficient to confidently distinguish a heterozygous locus from a homozygous locus. There were 3819 (42.0%) cases in which lobSTR exclusively assigned a genotype using only a single read. For the remaining repeats genotyped by lobSTR and not the present system, manual inspection revealed that the present system failed to genotype many of these repeats because it could not assign a high enough confidence (>50%) to the genotype. Finally, there were 417,097 (10.3%) repeats not genotyped by either method primarily because no reads could be mapped to these regions. In all, the present system assigns genotypes to ~90% of repeats in the HG01140 genome, and in the cases where both methods make a call, the concordance in genotypes is ~90%. Although the discordant genotypes were not exhaustively validated, no evidence was seen to suggest that lobSTR generally assigns genotypes more accurately than the present system.

Discussion

Repetitive DNA sequences pose unique challenges to next-generation sequencing technologies. However, these sequences are too important to ignore, in terms of their frequent occurrence in the genome and their biological relevance. The present system uses properties of reference repeat sequences and the reads that map to them, to best identify reads that contribute to true alleles. To enable accurate calls, the present example first evaluated several methods for mapping repeat-containing reads to the human reference sequence. It was found that when reads were filtered by mapping quality, Novoalign and Bowtie2 correctly map >93% of simulated repeat-containing reads to the human reference (compared with 3% mapped by lobSTR) while maintaining an inaccuracy rate that is lower than lobSTR. Filtering reads by mapping quality allowed for optimizing the trade-off of maximizing correctly mapped reads while minimizing the incorrectly mapped reads.

When the HG01140 genome from the 1000 Genomes Project was analyzed, it was found that the present system assigned genotypes to ~90% of the repeats, whereas lobSTR genotyped <3%. The disparity between the methods results likely from the difference in how many reads are mapped by lobSTR and Novoalign. LobSTR did make calls that the present system missed for 9,093 (8.57%) repeats. Of these calls that the present system missed, 42% were made with the support of a single read. The present system required the support of two reads to make calls in diploid genomes. From the remaining cases, the present system sometimes failed to have high enough genotype probabilities (>50%), and in other cases, lobSTR was able to exclusively make a call likely because it was able to map more reads to the locus. There is no doubt that there are cases in which lobSTR will excel at assigning genotypes, particularly those that exhibit extreme allelic variation from the reference (such as in the case of expanded repeats at the HTT locus in Huntington's patients); however, based on the number of calls, ~90% concordance in genotypes for repeats in which both methods made a call and the Sanger validation data, the present system offers the best comprehensive approach for exhaustively genotyping repeats in human genomes.

The present system implemented as software can be multithread and scales well on multi-core processors. An analysis of ~4 million reference repeats in the NA12878 genome (40× post-processed coverage, 100 bp reads) takes 11 h using a single core of an AMD Opteron 6174 CPU and a maximum of 1.65 GB of memory. With 48 cores, the runtime is reduced to 20 min. Runtimes can be further reduced by opting to generate only the VCF output. In addition to outputting genotypes using VCF, the present system optionally produces a detailed report that includes an annotated alignment of all the reads to the reference sequence for each microsatellite locus. It is envisioned that this extended report will be valuable for manually confirming calls and for further refining the method. The use of VCF output ensures the compatibility of the present system with other variant callers and analysis pipelines. For example, the VCF output of the present system can be used to augment indel calls from GATKs UnifiedGenotyper to provide a comprehensive and more accurate set of variant calls.

CITED REFERENCES

1000 Genomes Project Consortium. A map of human genome variation from population-scale sequencing. Nature. 2010; 467:1061-1073.

Albers C A, Lunter G, Macarthur D G, McVean G, Ouwehand W H, et al. Dindel: Accurate indel calls from short-read data. Genome research. 2011; 21:961-973.

Albrecht A, Mundlos S. The other trinucleotide repeat: polyalanine expansion disorders. Curr. Opin. Genet. Dev. 2005; 15:285-293.

Albrecht A N, Kornak U, Boddrich A, Suring K, Robinson P N, et al. A molecular pathogenesis for transcription factor associated poly-alanine tract expansions. Human molecular genetics. 2004; 13:2351-2359.

Altshuler D M, Gibbs R A, Peltonen L, Dermitzakis E, Schaffner S F, et al. Integrating common and rare genetic variation in diverse human populations. Nature. 2010; 467:52-58.

Axford M M, Lopez-Castel A, Nakamori M, Thornton C A, Pearson C E. Replacement of the myotonic dystrophy type 1 CTG repeat with 'non-CTG repeat' insertions in specific tissues. Journal of medical genetics. 2011; 48:438-443.

Bashir A, Volik S, Collins C, Bafna V, Raphael B J. Evaluation of paired-end sequencing strategies for detection of genome rearrangements in cancer. PLoS computational biology. 2008; 4:e1000051.

Benson G. Tandem repeats finder: a program to analyze DNA sequences. Nucleic acids research. 1999; 27:573-580.

Challis D, Yu J, Evani U S, Jackson A R, Paithankar S, Coarfa C, Milosavljevic A, Gibbs R A, Yu F. An integrative variant analysis suite for whole exome next-generation sequencing data. BMC Bioinformatics. 2012; 13:8.

Danecek P, Auton A, Abecasis G, Albers C A, Banks E, DePristo M A, Handsaker R E, Lunter G, Marth G T, Sherry S T, et al. The variant call format and VCFtools. Bioinformatics. 2011; 27:2156-2158.

DePristo M A, Banks E, Poplin R, Garimella K V, Maguire J R, Hartl C, Philippakis A A, del Angel G, Rivas M A, Hanna M, et al. A framework for variation discovery and genotyping using next-generation DNA sequencing data. Nat. Genet. 2011; 43:491-498.

Douglas J A, Skol A D, Boehnke M. Probability of detection of genotyping errors and mutations as inheritance inconsistencies in nuclear-family data. Am. J. Hum. Genet. 2002; 70:487-495.

Durbin R M, Abecasis G R, Altshuler D L, Auton A, Brooks L D, et al. A map of human genome variation from population-scale sequencing. Nature. 2010; 467:1061-1073.

Ewing B, Hillier L, Wendl M C, Green P. (1998): Base-calling of automated sequencer traces using phred. I. Accuracy assessment. Genome Res. 8(3):175-185.

Ewing B, Green P. (1998): Base-calling of automated sequencer traces using phred. II. Error probabilities. Genome Res. 8(3):186-194.

Fondon J W, III, Martin A, Richards S, Gibbs R A, Mittelman D. Analysis of microsatellite variation in *Drosophila melanogaster* with population-scale genome sequencing. PLoS One. 2012; 7:e33036.

Fondon J W, 3rd, Mele G M, Brezinschek R I, Cummings D, Pande A, et al. Computerized polymorphic marker identification: experimental validation and a predicted human polymorphism catalog. Proceedings of the National Academy of Sciences of the United States of America. 1998; 95:7514-7519.

Fonville N C, Ward R M, Mittelman D. Stress-induced modulators of repeat instability and genome evolution. J. Mol. Microbiol. Biotechnol. 2011; 21:36-44.

Ge J, Eisenberg A, Budowle B. Developing criteria and data to determine best options for expanding the core CODIS loci. Investig. Genet. 2012; 3:1.

Gemayel R, Vinces M D, Legendre M, Verstrepen K J. Variable tandem repeats accelerate evolution of coding and regulatory sequences. Annual review of genetics. 2010; 44:445-477.

Gerber H P, Seipel K, Georgiev O, Hofferer M, Hug M, et al. Transcriptional activation modulated by homopolymeric glutamine and proline stretches. Science. 1994; 263:808-811.

Glen C D, Dubrova Y E. Exposure to anticancer drugs can result in transgenerational genomic instability in mice. Proc. Natl. Acad. Sci. USA. 2012; 109:2984-2988.

Gymrek M, Golan D, Rosset S, Erlich Y. lobSTR: a short tandem repeat profiler for personal genomes. Genome Res. 2012; 22:1154-1162.

Hannan A J. Tandem repeat polymorphisms: modulators of disease susceptibility and candidates for 'missing heritability'. Trends in genetics: TIG. 2010; 26:59-65.

Highnam G, Franck C, Martin A, Stephens C, Puthige A, Mittelman D. Accurate human microsatellite genotypes from high-throughput resequencing data using informed error profiles. Nucleic Acids Res. 2013 Jan. 7; 41(1):e32.

Hile S E, Eckert K A. DNA polymerase kappa produces interrupted mutations and displays polar pausing within mononucleotide microsatellite sequences. Nucleic acids research. 2008; 36:688-696.

Kelkar Y D, Strubczewski N, Hile S E, Chiaromonte F, Eckert K A, et al. What is a microsatellite: a computational and experimental definition based upon repeat mutational behavior at A/T and GT/AC repeats. Genome biology and evolution. 2010; 2:620-635.

Korol A, Rashkovetsky E, Iliadi K, Nevo E. *Drosophila* flies in "Evolution Canyon" as a model for incipient sympatric speciation. Proc Natl Acad Sci USA. 2006; 103:18184-18189.

Langmead B, Salzberg S L. Fast gapped-read alignment with Bowtie 2. Nat. Methods. 2012; 9:357-359.

Lango Allen H, Estrada K, Lettre G, Berndt S I, Weedon M N, et al. Hundreds of variants clustered in genomic loci and biological pathways affect human height. Nature. 2010; 467:832-838.

Legendre M, Pochet N, Pak T, Verstrepen K J. Sequence-based estimation of minisatellite and microsatellite repeat variability. Genome Res. 2007; 17:1787-1796.

Li H, Durbin R. Fast and accurate long-read alignment with Burrows-Wheeler transform. Bioinformatics. 2010; 26:589-595.

Li H, Handsaker B, Wysoker A, Fennell T, Ruan J, Homer N, Marth G, Abecasis G, Durbin R. The Sequence Alignment/Map format and SAMtools. Bioinformatics. 2009; 25:2078-2079.

Li H, Homer N. A survey of sequence alignment algorithms for next-generation sequencing. Brief. Bioinform. 2010; 11:473-483.

Li H, Durbin R. Fast and accurate short read alignment with Burrows-Wheeler transform. Bioinformatics. 2009; 25:1754-1760.

Li H, Ruan J, Durbin R. Mapping short DNA sequencing reads and calling variants using mapping quality scores. Genome research. 2008; 18:1851-1858.

Loeb L A, Loeb K R, Anderson J P. Multiple mutations and cancer. Proc. Natl. Acad. Sci. USA. 2003; 100:776-781.

Lopez Castel A, Cleary J D, Pearson C E. Repeat instability as the basis for human diseases and as a potential target for therapy. Nat. Rev. Mol. Cell Biol. 2010; 11:165-170.

Lunter G, Goodson M. Stampy: a statistical algorithm for sensitive and fast mapping of Illumina sequence reads. Genome Res. 2011; 21:936-939.

Lynch H T, Lynch P M, Lanspa S J, Snyder C L, Lynch J F, et al. Review of the Lynch syndrome: history, molecular genetics, screening, differential diagnosis, and medicolegal ramifications. Clinical genetics. 2009; 76:1-18.

Mackay T F C, Richards S, Stone E A, Barbadilla A, Ayroles J F, Zhu D, Casillas S, Han Y, Magwire M M, Cridland J M, et al. The *Drosophila melanogaster* Genetic Reference Panel. Nature. 2012; 482:173-178.

Manolio T A, Collins F S, Cox N J, Goldstein D B, Hindorff L A, et al. Finding the missing heritability of complex diseases. Nature. 2009; 461:747-753

Margulies M, Egholm M, Altman W E, Attiya S, Bader J S, et al. Genome sequencing in microfabricated high-density picoliter reactors. Nature. 2005; 437:376-380.

McIver L J, Fondon J W, 3rd, Skinner M A, Garner H R. Evaluation of microsatellite variation in the 1000 Genomes Project pilot studies is indicative of the quality and utility of the raw data and alignments. Genomics. 2011; 97:193-199

Mills R E, Luttig C T, Larkins C E, Beauchamp A, Tsui C, et al. An initial map of insertion and deletion (INDEL) variation in the human genome. Genome research. 2006; 16:1182-1190.

Mills R E, Walter K, Stewart C, Handsaker R E, Chen K, et al. Mapping copy number variation by population-scale genome sequencing. Nature. 2011; 470:59-65.

Mills R E, Pittard W S, Mullaney J M, Farooq U, Creasy T H, et al. Natural genetic variation caused by small insertions and deletions in the human genome. Genome research. 2011; 21:830-839

Mirkin S M. Expandable DNA repeats and human disease. Nature. 2007; 447:932-940.

Mittelman D, Moye C, Morton J, Sykoudis K, Lin Y, et al. Zinc-finger directed double-strand breaks within CAG repeat tracts promote repeat instability in human cells. Proceedings of the National Academy of Sciences of the United States of America. 2009; 106:9607-9612.

Orr H T. Unstable nucleotide repeat minireview series: a molecular biography of unstable repeat disorders. The Journal of biological chemistry. 2009; 284:7405.

Reuschenbach M, Kloor M, Morak M, Wentzensen N, Germann A, et al. Serum antibodies against frameshift peptides in microsatellite unstable colorectal cancer patients with Lynch syndrome. Familial cancer. 2010; 9:173-179.

Sainudiin R, Durrett R T, Aquadro C F, Nielsen R. Microsatellite mutation models: insights from a comparison of humans and chimpanzees. Genetics. 2004; 168:383-395.

Sawyer L A, Hennessy J M, Peixoto A A, Rosato E, Parkinson H, et al. Natural variation in a *Drosophila* clock gene and temperature compensation. Science. 1997; 278: 2117-2120.

Schug M D, Mackay T F, Aquadro C F. Low mutation rates of microsatellite loci in *Drosophila melanogaster*. Nature genetics. 1997; 15:99-102.

TCGA. Comprehensive genomic characterization defines human glioblastoma genes and core pathways. Nature. 2008; 455:1061-1068.

Verstrepen K J, Jansen A, Lewitter F, Fink G R. Intragenic tandem repeats generate functional variability. Nature genetics. 2005; 37:986-990.

Wells R D, Dere R, Hebert M L, Napierala M, Son L S. Advances in mechanisms of genetic instability related to hereditary neurological diseases. Nucleic acids research. 2005; 33:3785-3798.

Vinces M D, Legendre M, Caldara M, Hagihara M, Verstrepen K J. Unstable tandem repeats in promoters confer transcriptional evolvability. Science. 2009; 324:1213-1216.

What is claimed is:

1. A method of genotyping comprising:
obtaining a sequence-read mapping, the sequence-read mapping comprising sequence reads from a subject polynucleotide sequence mapped to a reference sequence;
selecting flanking reads from the sequence reads, wherein each flanking read spans a repeat in the reference sequence in addition to one or more flanking bases on each of two ends of the repeat, and wherein the selecting the flanking reads from the sequence reads results in a flanking-read mapping comprising the repeat and the flanking reads that map thereto;
extracting sequence attributes from the flanking-read mapping, the sequence attributes comprising at least repeat length, repeat unit size, repeat purity, and average base quality score of the flanking read;
associating the extracted sequence attributes with a genotyping error rate, comprising matching the extracted sequence attributes with one of a plurality of bins of partitioned sequence attribute values with known, corresponding genotyping error rates, each bin encompassing a single, known corresponding genotyping error rate for a range of sequence attribute values for each of repeat length, repeat unit size, repeat purity, and average base quality score of the flanking read;
calculating a genotype probability for each flanking read from the genotyping error rate; and
assigning a genotype to the subject polynucleotide sequence based on the genotype probabilities calculated for the flanking reads.

2. The method of claim 1 wherein the genotype comprises a repeat length.

3. The method of claim 1 wherein the obtaining the sequence-read mapping comprises mapping the sequence reads from the subject polynucleotide sequence to the reference sequence.

4. The method of claim 1 wherein the obtaining the sequence-read mapping comprises mapping the sequence reads from the subject polynucleotide sequence to the reference sequence and then locally realigning the aligned sequence reads around indel-containing regions.

5. The method of claim 1 wherein the obtaining the sequence-read mapping comprises sequencing the subject polynucleotide sequence to obtain the sequence reads and mapping the sequence reads to the reference sequence.

6. The method of claim 1 wherein the obtaining the sequence-read mapping comprises sequencing the subject polynucleotide sequence to obtain the sequence reads; mapping the sequence reads from the subject polynucleotide sequence to the reference sequence; and then locally realigning the aligned sequence reads around indel-containing regions.

7. A system for genotyping comprising a processor configured to:
obtain a sequence-read mapping, the sequence-read mapping comprising sequence reads from a subject polynucleotide sequence mapped to a reference sequence;
select flanking reads from the sequence reads, wherein each flanking read spans a repeat in the reference sequence in addition to one or more flanking bases on each of two ends of the repeat, and wherein the selecting the flanking reads from the sequence reads results in a flanking-read mapping comprising the repeat and the flanking reads that map thereto;
extract sequence attributes from the flanking-read mapping, the sequence attributes comprising at least repeat length, repeat unit size, repeat purity, and average base quality score of the flanking read;
associate the extracted sequence attributes with a genotyping error rate, wherein the processor is configured to associate the extracted sequence attributes with one of a plurality of bins of partitioned sequence attribute values with known, corresponding genotyping error rates, each bin encompassing a single, known corresponding genotyping error rate for a range of sequence attribute values for each of repeat length, repeat unit size, repeat purity, and average base quality score of the flanking read;
calculate a genotype probability for each flanking read from the genotyping error rate; and
assign a genotype to the subject polynucleotide sequence based on the genotype probabilities calculated for the flanking reads.

8. The system of claim 7 wherein the genotype comprises a repeat length.

* * * * *